United States Patent
Hammond et al.

(10) Patent No.: US 6,255,051 B1
(45) Date of Patent: Jul. 3, 2001

(54) MULTIPLE SEQUENTIAL POLYNUCLEOTIDE DISPLACEMENT REACTIONS FOR SIGNAL AMPLIFICATION AND PROCESSING

(75) Inventors: Philip W. Hammond, Brighton; Ezra S. Abrams, West Newton; T. Christian Boles, Waltham; Andrew R. Muir, Cohasset, all of MA (US)

(73) Assignee: Mosaic Technologies Inc., Waltham, MA (US)

( * ) Notice: Subject to any disclaimer, the term of this patent is extended or adjusted under 35 U.S.C. 154(b) by 0 days.

(21) Appl. No.: 09/188,086

(22) Filed: Nov. 6, 1998

Related U.S. Application Data

(60) Provisional application No. 60/064,667, filed on Nov. 6, 1997.

(51) Int. Cl.[7] .............................. C07H 21/04; C07H 19/04
(52) U.S. Cl. .................... 435/6; 536/25.32; 536/25.4; 536/25.6; 536/26.6
(58) Field of Search ................... 435/6; 536/25.32, 536/25.4, 25.6, 26.5

(56) References Cited

U.S. PATENT DOCUMENTS

| | | | |
|---|---|---|---|
| 4,725,536 | 2/1988 | Fritsch, et al. | 435/6 |
| 4,766,062 | 8/1988 | Diamond et al. | 435/6 |
| 4,766,064 | 8/1988 | Williams et al. | 435/6 |
| 4,829,098 | 5/1989 | Hoffman et al. | 522/5 |
| 5,034,428 | 7/1991 | Hoffman et al. | 522/5 |
| 5,215,882 | 6/1993 | Bahl et al. | 435/6 |
| 5,237,016 | 8/1993 | Ghosh et al. | 525/329.4 |
| 5,310,650 | 5/1994 | McMahon et al. | 435/6 |
| 5,482,836 | 1/1996 | Cantor et al. | 435/6 |
| 5,610,287 | 3/1997 | Nikiforov et al. | 536/24.3 |
| 5,679,524 | 10/1997 | Nikiforov et al. | 435/6 |
| 5,741,639 | 4/1998 | Ensing et al. | 435/6 |

FOREIGN PATENT DOCUMENTS

| | | | |
|---|---|---|---|
| 0 269 764 A1 | 12/1986 | (EP) | C12Q/1/68 |
| 0 330 185 | 8/1989 | (EP) | |
| 0 450 370 A1 | 10/1991 | (EP) | C12Q/1/68 |
| 0 450 594 A2 | 10/1991 | (EP) | C12Q/1/68 |
| 0 671 626 A1 | 9/1995 | (EP) | G01N/33/543 |
| 0 703 296 A1 | 3/1996 | (EP) | C12Q/1/68 |
| H3-47097 | 2/1991 | (JP) | C12Q/1/68 |
| WO 87/03911 | 7/1987 | (WO) | C12Q/1/68 |
| WO 90/0758 | 7/1990 | (WO) | C12Q/1/68 |
| WO 91/08307 | 6/1991 | (WO) | C12Q/1/68 |
| WO 92/15712 | 9/1992 | (WO) | C12Q/1/68 |
| WO 94/06937 | 3/1994 | (WO) | C12Q/1/68 |
| WO 94/09156 | 4/1994 | (WO) | C12Q/1/68 |
| WO 94/16108 | 7/1994 | (WO) | C12Q/1/68 |
| WO 96/00795 | 1/1996 | (WO) | C12Q/1/68 |
| WO 97/27327 | 7/1997 | (WO) | C12Q/1/68 |
| WO 97/35033 | 9/1997 | (WO) | C12Q/1/68 |
| WO 97/41256 | 11/1997 | (WO) | C12Q/1/68 |
| WO 97/45554 | 12/1997 | (WO) | C12Q/1/68 |
| WO 97/45721 | 12/1997 | (WO) | G01N/27/447 |

OTHER PUBLICATIONS

Biagioni, et al., "A New Method for the Preparation of DNA–Cellulose", *Analytical biochemistry*, Academic Press, Inc. 89, 616–619 (1978).

Baba, et al., "Base–specific separation of oligodeoxynucleotides by capillary affinity gel electrophoresis", *Electrophoresis*, 19, 433–436 (1998).

(List continued on next page.)

*Primary Examiner*—Eggerton A. Campbell
*Assistant Examiner*—Joyce Tung
(74) *Attorney, Agent, or Firm*—Hamilton, Brook, Smith & Reynolds, P.C.

(57) ABSTRACT

Methods for determining the presence of a target polynucleotide sequence using chemical hybridization in sequential probe and displacement complex formation with potential for signal gain prior to detection are disclosed.

57 Claims, 11 Drawing Sheets

OTHER PUBLICATIONS

Igloi, Gabor L., "Variability in the stability of DNA–peptide nucleic acid (PNA) single–base mismatched duplexes: Real-time hybridization during affinity electrophoresis in PNA-containing gels", Proc. Natl. Acad. Sci. USA, vol. 95, pp. 8562–8567, Jul. 1998. Biochemistry.

Jarrett, Harry W., "Affinity chromatography with nucleic acid polymers", Journal of Chromatography, 618, pp. 315–339, 1983. biomedical Applications, Elsevier Science Publishers B.V. Amsterdam.

Muscate, et al., "Capillary Affinity Gel Electrophoresis for Combined Size–and Sequence–Dependent Separation of Oligonucleotides", Anal. Chem. 70, pp. 1419–1424,1998.

Ness, Jeffrey Van, "A versatile solid support system for oligodeoxynucleotide probe–based hybridization assays", Nucleic Acids Research, Oxford University Press, vol. 19, No. 12, pp. 3345–3350, 1991.

Nielsen, Peter E., "Sequence–Selective Recognition of DNA by Strand Displacement with a Thymine–Substituted Polyamide", Science, vol. 254, pp. 1497–1500,1991.

Olejnik, et al., "Photocleavable aminotag phosphoramidites for 5'—termini DNA/RNA labeling", Nucleic Acids Research, Oxford University Press, vol. 26, No. 15, pp. 3572–3576, 1998.

Ozaki, et al., "Affinity capillary electrophoresis using DNA conjugates", Nucleic Acids Symposium Series, Oxford University Press, No. 37, pp. 235–236, 1997.

Quartin, Robin S. and Wetmur, James G., "Effect of Ionic Strength on the Hybridization of Oligodeoxynucleotides with Reduced Charge Due to Methylphosphonate Linkages to Unmodified Oligodeoxynucleotides Containing the Complementary Sequence", Biochemistry 28, pp. 1040–1047, 1989. American Chemical Society.

Reinhartz, et al., "A novel rapid hybridization technique: paper chromatography hybridization assay (PACHA)", Elsevier Science Publishers B.V., pp.221–226, 1993.

Timofeev, et al., "Regioselective immobilization of short oligonucleotides to acrylic copolymer gels", Nucleic Acids Research, Oxford University Press, vol. 24, No. 16, pp. 3142–3148, 1996.

Tsurui, et al., "A rapid and efficient cloning method with a solid–phase DNA probe: application for cloning the 5' Flanking region of the gene encoding human fibronectin", Elsevier Science Publishers B.F. (Biomedical Division), pp.233–239, 1990.

Wieder, Robert and Wetmur, James G., "One Hundred–fold Acceleration of DNA Renaturation Rates in Solution", Biopolymers, John Wiley and Sons, Inc., vol. 20, 1537–1547, 1981.

Wetmur, James G., "Acceleration of DNA Renaturation Rates", Biopolymers, John Wiley and Sons, Inc., vol. 14., 2517–2524, 1975.

Wetmur, James G., "DNA Probes: Applications of the Principles of Nucleic Acid Hybridization", Critical Reviews in Biochemistry and Molecular Biology, CRC Press, Inc., 26(3/4) :227–259, 1991.

Yokota, Hiroshi and Oishi, Michio, "Differential cloning of genomic DNA: Cloning of DNA with an altered primary structure by in–gel competitive reassociation", Proc. Natl. Acad. USA, vol. 87, pp.6398–6402, 1990. Biochemistry.

Vary, C.P.H., "A homogeneous nucleic acid hybridization assay based on strand displacement," *Nucleic Acids Research*, 15(17) :6883–6897 (1987).

Vary, C.P.H., et al., "Nonisotopic Dectection Methods for Strand Displacement Assays of Nucleic Acids," *Clin. Chem.* 32 (9) :1696–1701 (1986).

US 6,255,051 B1

MULTIPLE SEQUENTIAL POLYNUCLEOTIDE DISPLACEMENT REACTIONS FOR SIGNAL AMPLIFICATION AND PROCESSING

RELATED APPLICATION(S)

This application is claiming priority to Provisional Application No. 60/064,667, filed on Nov. 6, 1997. The entire teachings of which are incorporated herein by reference.

BACKGROUND OF THE INVENTION

The principle of hybridization serves as the basis upon which methods of detecting nucleic acids is founded. Conventional methods for detecting the presence of a particular nucleic acid sequence involves employing a complementary sequence, the probe sequence which is usually labeled, and incubating this labeled sequence with the sample putatively containing the sample of interest. If the polynucleotide sequence of the target nucleic acid is complementary to the polynucleotide sequence of the probe, then the two (under suitable conditions) will hybridize. If there is hybridization, then the hybridization complex can be detected. Variations of this general protocol have been developed over time. Sensitivity of the detection assay is critical especially when detecting the presence of nucleic acids that are in low concentrations.

To improve the sensitivity in nucleic acid assays, different methods of amplification have developed. One approach is to amplify the number of target molecules. Polymerase Chain Reaction, or PCR, is such a method that is employed to increase the copy number of a target polynucleotide sequence which results in the amplification of the original target sequence. Ausubel, F. M., et al. (eds.), *Current Protocols in Molecular Biology,* Green Publishing Associates and Wiley-Interscience, 5$^{th}$ ed., (1991), vol. 2, pp. 15.1.1–15.3.8.; 15.4.1–15.4.6. Strand Displacement Amplification (SDA) and Transcription Mediated Amplification (TMA) are two other examples of methods that are used to increase or amplify the target polynucleotide sequence. All of these methods require proteins, for example, the enzymes that are used in these procedures to catalyze the necessary reactions, which constrain the conditions under which the assay can be performed. Due to the necessary presence of these enzymes in these particular assays, critical and stringent reactions must be established and maintained to insure the efficacy of these stated methods.

It would be desirable to have a nucleic acid hybridization assay that is sensitive enough to amplify a signal that is generated during a hybridization-displacement assay rather than the target sequence itself, yet avoids the above-mentioned complications.

SUMMARY OF THE INVENTION

The invention pertains to novel and commercially useful methods for analyzing nucleic acids. The present invention provides for a highly specific hybridization-based identification system of nucleic acids using multiple sequential polynucleotide displacement reactions which result in gain or amplification of a detectable signal.

The core of the present invention provides multiple rounds of polynucleotide displacement wherein the displaced polynucleotide of the preceeding displacement reaction is transferred to contact the next probe complex where it becomes the target for a new cycle of displacement.

In one embodiment of the invention, a method of detecting a target polynucleotide sequence within a biological sample is disclosed. This detection method involves a series of sequential hybridization and displacement reactions, that utilize probe complexes formed by hybridization between complementary polynucleotide sequences which are hybridized to one another to form a probe complex. This hybridization complex is subsequently contacted with a polynucleotide sequence which will compete with one of the constituent polynucleotide sequences of the complex. The target nucleotide sequence is one such sequence that will compete off one the constituents found in the probe complex, generally the first probe complex formed. This competition results in the generation of a displaced polynucleotide sequence. Based on the physicochemical principle of affinity, the competing polynucleotide sequence will displace one of the two polynucleotide sequences comprising the probe complex. The displaced polynucleotide sequence(s) then serve, as a signal which can be detected in any number of ways, or be used to compete off another constituent polynucleotide sequence in a different probe complex. Multiple displacement can be least one or more displacement events other performed with, or without gain, of signal at each displacement step.

In another embodiment, the present invention pertains to a method of detecting a target polynucleotide sequence within a biological test sample using a recursive cycle. Several cycles of probe and displacement complex formation generating multiple displacement polynucleotide sequences in which one of these displaced polynucleotide sequences is identical to the original target polynucleotide sequence, thereby facilitating cycling back to the first displacement complex and proceeding through the sequential hybridization and displacement cycles again. This process of recycling through probe and displacement complex formation provides for the amplification of the assay signal(s) prior to detection.

In another embodiment of the invention, a method for detecting a target polynucleotide sequence in a nucleic acid molecule within a sample using a set of heterogenous signals is described. In this embodiment, cycles of hybridization and displacement take place in which a bifurcation event occurs resulting in the production of multiple and distinct hybridization/displacement cycles, thereby generating multiple heterogenous signals for one particular target polynucleotide sequence.

In still another embodiment, the invention pertains to a method of detecting different target polynucleotide sequences in one sample by generating a homogenous signal. Probe complexes are formed by hybridizing a first polynucleotide sequence, that is partially or completely complementary to the target polynucleotide sequence, with a second polynucleotide sequence (which is separate and distinct from the target sequence). This probe complex formation occurs for all of the target polynucleotide sequences to be analyzed in the sample. Hybridization and displacement cycles take place independently using different target polynucleotide sequences designated for analysis. However, the assay is constructed in such a way as to generate a homogenous polynucleotide sequence signal that accounts for all of the target polynucleotide sequences analyzed.

In another embodiment, the invention pertains to a method for detecting a target polynucleotide sequence in a nucleic acid molecule using an immobilizing surface. Cycles of hybridization and displacement occur throughout this method. However, the hybridization complexes are immobilized to a surface and the displaced polynucleotide sequence is free in solution. The displaced polynucleotide sequence liberated from a hybridization complex, in particular, a displacement complex by employing a competing polynucleotide sequence to displace a polynucleotide sequence constituent of the complex, can be transferred to another surface in order to continue the reaction cycles, for example, another displacement complex. The surfaces involved can be coextensive or can be separated from each other by, for example, size-exclusion membranes. Alternatively, the surfaces can be spatially separated as exemplified by using different conical tubes as representing different surfaces. This embodiment also embraces the use of solid support matrixes in which reaction stations can be integral to the matrix itself. The reactants for a particular event, such as probe complex or displacement complex formation, can be placed into these reaction stations, thereby isolating these individual reaction events. Movement of reaction substrates or products from one station to the next can be accomplished via assisted or unassisted migration through the matrix, or alternatively, mechanical transfer using, for example, a pipette.

A diagnostic kit for determining the presence of a target polynucleotide sequence within a biological sample is also disclosed in the present invention. The kit comprises a first probe complex and at least one second probe complexes. The first probe complex comprises a first polynucleotide sequence comprising a sequence complementary to a target polynucleotide sequence, hybridized to a second polynucleotide sequence. The second probe complex comprises a third polynucleotide sequence, comprising a sequence complementary to the second polynucleotide sequence of the first probe complex, hybridized to a labeled fourth polynucleotide sequence.

Thus, based on the displacement reactions described herein, novel methods are now available for the accurate and sensitive detection of the presence of small quantities of polynucleotide sequences present in a biological sample. Assays based on hybridization are very specific and are fairly easy to perform. Also, they proceed robustly under a relatively wide range of experimental conditions. Displacement allows more convenient and sensitive detection of hybridization reactions by allowing efficient removal of the displaced polynucleotide sequence, which is used to generate a signal, from the unhybridized probe complexes. Enzymatic-based assays are very sensitive, however, these assays require very stringent control of assay conditions to ensure proper enzymatic activity.

The present invention overcomes limitations presented by enzymatic-based assays. There are other practical benefits to the current invention. The invention provides methods of signal generation and amplification which depends on hybridization but not enzymatic catalysis. The invention provides methods of processing signals from hybridization reactions so that one target polynucleotide sequence can generate multiple spatially or chemically distinguishable signals. Likewise, the invention provides methods for converting signals generated by hybridization of different target polynucleotide sequences into a common homogenous signal.

DETAILED DESCRIPTION OF THE INVENTION

Figure 1A:
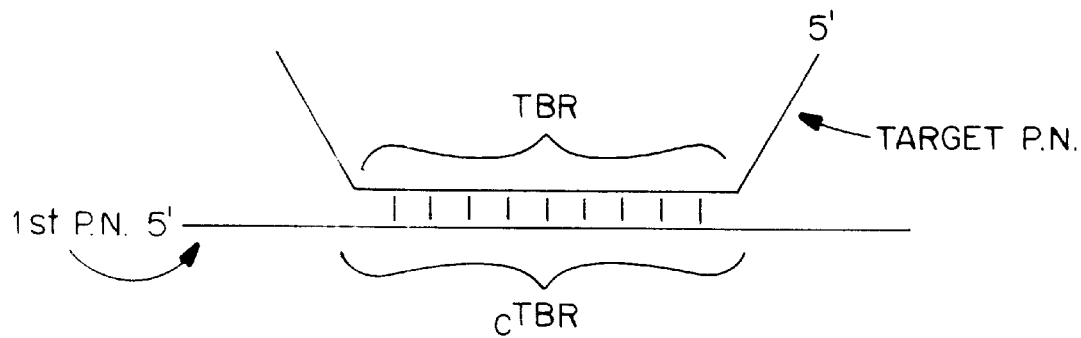
FIG. 1a is a schematic representation of the polynucleotides used in the present invention.

The present invention pertains to novel methods for analyzing nucleic acids in a biological sample. The methods described herein provide for a highly specific hybridization-based identification system of nucleic acids with gain or amplification of a chemical signal prior to detection. This chemical signal can be detected by numerous means as described herein. The methods disclosed herein are based on the physical chemistry of hybridization between nucleic acids or polynucleotide sequence containing molecules without the involvement of enzymes in the assay. This is accomplished by designing probe complexes so that all target polynucleotide sequences and displaced polynucleotide sequences displace more than one polynucleotide sequence from the probe complexes with which they react. Thus, exponential signal amplification systems with virtually any (two, three, four-fold, etc.) Signal gain per displacement cycle can be constructed. Linear amplification is also encompassed by the present invention. By repeating displacement cycles the assay signal generated is reproduced with each pass of an assay cycle.

As used herein, "biological sample" includes any sample that contains nucleic acids. For example, blood, urine, other bodily fluids, cells (both plant and animal), cell extract, tissues and tissue extract are within the scope of the present invention.

The nucleic acids of the present invention include deoxyribonucleic acid (hereinafter, "DNA"), ribonucleic acid (hereinafter, "RNA"), modified nucleic acids, and nucleic acid analogs such as peptide nucleic acid ("PNA") and morpholino nucleic acids. Roth single stranded and double stranded nucleic acids are embraced by this invention. Higher ordered structures of nucleic acids, for example, RNA that has folded upon its linear strand forming a secondary loop structure, are also within the scope of the present invention. Polynucleotide sequences as used herein denote a nucleotide sequence from about 5 to about 50,000 nucleotides in length. There is no absolute length requirement for participating target polynucleotide sequence(s), however, a preferred range is from about 5 to about 1000. Preferably, the probe and displacing polynucleotide sequence(s) are from about 5 to about 1000 in nucleotide length. Most preferably, the probe and displacing nucleotide sequence(s) are from about 5 to about 100 in nucleotide length. One of ordinary skill in the art will be able to determine the appropriate length of nucleotide sequence to employ for the polynucleotides of the present invention. It should also be understood that the polynucleotide sequences of the present invention can be embedded within longer strands of nucleic acids or associated with other molecules.

Base-pairing is generally understood to occur in an antiparallel manner, however, there are occasions in which base-pairing can occur in a parallel fashion and this arrangement is also within the scope of the present invention. Base-pairing itself is understood to essentially follow a complementary pattern wherein a purine pairs with a pyrimidine via hydrogen bonds. More particularly, it is understood that complementary base-pairing of individual base pairs generally follows Chargaff's Rule wherein an adenine pairs with a thymine (or uracil) and guanine pairs with cytosine. However, there are modified bases which account for unconventional base-pairing. A modified nucleic acid is understood to mean herein a DNA or RNA nucleic acid molecule that contains chemically modified nucleotides. The term "nucleic acid analogue" is understood herein to denote non-nucleic acid molecules such as "PNA" and morpholino that can engage in base-pairing interactions with conventional nucleic acids. These modified bases and nucleic acid analogues are considered to be within the scope of the instant invention. For example, nucleotides containing deazaguaine and uracil bases can be used in place of guanine and thymine, respectively, to decrease the thermal stability of hybridized probes. Similarly, 5-methylcytosine can be substituted for cytosine in hybrids if increased thermal stability is desired. Modification to the sugar moiety can also occur and is embraced by the present invention. For example, modification to the ribose sugar moiety through the addition of 2'-O-methyl groups which can be used to reduce the nuclease susceptibility of RNA molecules. Modifications occurring with different moieties of the nucleic acid backbone are also within the scope of this invention. For example, the use of methyl phosphate, methyl phosphonate or phosphorothioate linkages to remove negative charges from the phosphodiester backbone can be used.

Hybridization is understood herein to mean admixing of at least two polynucleotide sequences under conditions suitable such that when at least two complementary polynucleotide sequences are present, they will then form a double-stranded structure through base-pairing. Mismatches are permitted in the instant invention. Nucleotide mismatch can affect the affinity between polynucleotide sequences. The greater the mismatch between polynucleotide sequences, generally the affinity is lower between them as compared to perfectly matched polynucleotide sequences. Generally, the greater the mismatch between polynucleotide sequences the easier it is to disrupt any hybridization that exists between them. When mismatches between base pairs are present, they generally account for no more than 5% of the region of base-pairing. Preferably, the degree of complementarity between hybridization partners is from about 100% to about 95%. If the melting temperature (Tm) of a hybridization complex containing mismatches is determined and comparing that Tm with the Tms of complexes with shorter lengths of perfectly matched nucleotides, the effective pairing length of complexes with mismatches can be determined and applied to the present invention.

The methods described herein comprise sequential steps involving the formation of hybridization complexes and displacement of polynucleotide sequences. In general the assay comprises the formation of a first probe complex by hybridizing polynucleotide sequences together, for example, a first and second polynucleotide sequence. This complex is then contacted by a competing polynucleotide sequence, for example, third polynucleotide sequence, forming a displacement complex. The target polynucleotide sequence is an example of a competing polynucleotide sequence. One of the polynucleotide sequence constituents of the probe complex, for example, the first polynucleotide sequence, has a higher affinity for the third polynucleotide sequence as compared to its hybridization partner, for example, the second polynucleotide sequence. Based on this affinity difference, the third polynucleotide sequence will displace the second polynucleotide sequence and bind to the first polynucleotide sequence. The displaced polynucleotide sequence, for example the second polynucleotide sequence, can then be employed as a competing polynucleotide sequence in a subsequent displacement reaction. The number of serial hybridization-displacement events will determine how many different species and number of polynucleotide sequences displaced and released from the hybridization complexes. The displaced polynucleotides from the second displacement reactions can then be employed as a complementary polynucleotide sequence in a subsequent third displacement reation, and repeated. Additionally, these free polynucleotide sequences, referred to herein as displaced polynucleotide sequences, can be used to generate a signal indicating the presence of the target polynucleotide sequence. These displaced polynucleotides can have bound to them a label that can be subject to detection. The label can be bound ionically, covalently, or via adsorption. Preferably, the label is bound covalently to any region of the nucleic acid comprising the polynucleotide sequence of interest which does not interfere with hybridizatiion. The label can include, but is not limited to, radioactive isotopes, such as a radioactive phosphorous atom, affinity reagents, such as biotin, intercalating fluorescent dyes, or a fluorescent moiety attached to the polynucleotide, peptides, enzymes, phosphoresent dyes or chelates, electrophores for detection by mass spectrometry, chemiluminescent moiety chromophores having strong absorbance.

Using a Photodyod Array (PDA) detector, a spectral analysis can be performed without the employment of any label per se. The polynucleotide sequence(s) that is being used to indicate the presence of a target polynucleotide sequence can be monitored and detected by its unique spectral image. An example of a PDA detector that can be used for the present invention is the PDA detector from Waters Corporation (Milford, Mass.). In the case of using a PDA or mass spectrometry, the displaced polynucleotide itself becomes the signal. Therefore, the requirement of attaching a label to the polynucleotide for detection becomes obsolete.

There are two types of hybridization complexes in the present invention, (i) the probe complex, and (ii) the displacement complex. A probe complex is understood herein to mean the product of a hybridization reaction of a first polynucleotide sequence and a second polynucleotide sequence. It is important to note that the term "first polynucleotide" is used throughout this description, however, as illustrated in the examples, "first" also denotes the order of the polynucleotide sequence in the assay method and can also mean more than one polynucleotide sequence. The polynucleotide sequences selected for this assay are chosen based upon their ability to hybridize to other polynucleotide sequences. There is no absolute length requirement for participating nucleic acids, however, a preferred range is from about 5 to about 1000. Preferably, the binding region between the polynucleotide sequences undergoing hybridization to form a probe complex is from about 5 to about 1000 nucleotides in length. In the first probe complex, the first polynucleotide sequence will have a degree of complementarity 95–100% with the target polynucleotide sequence, while the second polynucleotide sequence will have sufficient complementarity with the first polynucleotide sequence 95–100% to facilitate chemical hybridization between the two. Additional probe complexes can be formed by hybridizing other polynucleotide sequences that share complementarity (i.e., 95%–100%) with one another. Generally, at least one constituent polynucleotide sequence of a probe complex is a full or partial sequence complement to a previously displaced polynucleotide sequence that was generated from a prior displacement complex, or a full or partial complement to a target polynucleotide sequence. The polynucleotide sequences to be used in design of probe complexes are defined by the sequence of the target, which is generally known from the literature or from previous sequencing work. Conditions for formation of probe complexes will vary based on the type of component polynucleotides used. For polynucleotides with standard phosphodiester backbones, the two polynucleotides are mixed in a buffered solution (pH preferably between 6 and 9) with monovalent cation present preferably between 0.1 M to 1.0 M, optionally including divalent cation at concentrations between 0.1 mM to 10 mM. Preferably the concentration of the first and second polynucleotides are present at concentrations of at least 0.1 µM. Lower concentrations can be used, but hybridization will be slower. Preferably, the second polynucleotide is present at greater concentration to ensure that all of the first polynucleotide is hybridized to second polynucleotide. Preferably, the second polynucleotide is present at two to four-fold excess over the first polynucleotide. The mixture is heated to a temperature greater than the Tm of the probe complex and then slow cooled to a temperature below the Tm of the probe complex at a rate slow enough to allow the hybridization reaction to be completed. For example, for most polynucleotides without heat-labile modifications, such as enzymes, the mixture can be heated to 90–95° C. and slow cooled to room temperature (approximately 25° C.) over a period of 1 to 2 hours.

A target polynucleotide sequence, or sometimes referred to herein as the "target third polynucleotide sequence", is meant herein to denote a target polynucleotide sequence present in the biological test sample that is the focus of a particular assay. In the present invention, a sample can have a heterogenous population of target polynucleotide sequences or a homogeneous population in the sample.

A displacement complex is defined herein to denote a reaction product in which the displacement or removal from a hybridization complex of at least one polynucleotide sequence has occurred. This complex is formed by the hybridization of two or more polynucleotide sequences. There is no absolute length requirement for participating nucleic acids, however, a preferred range for DNA molecules is from about 9 to about 50 nucleotides in length. For other types of nucleic acids, the size range can be smaller or larger depending on their stability relative to DNA-DNA duplexes. The size of duplex region required to achieve a desired level of stability can be determined semi-empirically (discussed below). Preferably, the binding region between the polynucleotide sequences undergoing hybridization to form a displacement complex is from about 5 to about 1000 nucleotides in length. The displacement complex is formed as a result of a previous probe complex coming in contact with a competing polynucleotide sequence. This competing polynucleotide sequence will compete off at least one constituent polynucleotide sequence that is intrinsic to the complex. The partner polynucleotide sequence of the competed off polynucleotide sequence has a higher affinity for the competing polynucleotide sequence, hence the displacement event o at least one polynucleotide sequence from the complex. Generally, the competing polynucleotide sequence will be either the target polynucleotide sequence or a displaced polynucleotide sequence that was displaced in a previous displacement complex reaction. However, the first probe complex is always contacted by the target polynucleotide sequence forming the first displacement complex, subsequent rounds of hybridization and displacement can involve other displaced polynucleotide sequences. Displacement reactions are carried out at temperatures substantially below the Tm of the probe complex so that spontaneous melting of the probe complex does not occur. Methods to determine this temperature are well known to those of skill in the art.

In general, it is preferred to design probe complexes that can hybridize and undergo displacement with target polynucleotides at room temperature. Generally, many single-stranded DNA and RNA targets can react with probe complexes composed of DNA or RNA at room temperature in a buffered solution (pH preferably between 6 and 9) with monovalent cation present preferably between 0.01 M to 1.0 M, optionally including divalent cations at concentrations between 0.1 mM to 10 mM, optionally including additives to inhibit nuclease activity such as detergents, surfactants, or chaotropes.

Occasionally, targets that exhibit intra-molecular base pairing may not productively react with the probe complex. In these cases, it may be useful to perform the displacement reactions at temperatures higher than room temperature, but substantially below the Tm of the probe complex, in order to melt out the intra-molecular base pairing that prevents productive hybridization with the probe complex. The product of this event is not only a new hybridization complex, but also, the displaced polynucleotide sequence which can then serve as a signal in the assay, alternatively, be used to displace another constituent polynucleotide sequence in a subsequent displacement complex.

The appropriate temperature to perform displacement reactions depends on the thermal stabilities of the hybrids present in the hybridization complex. Any spontaneous dissociation of the displaced polynucleotide sequence will initiate signal generation in subsequent hybridization-displacement events and give rise to target-independent signals (noise). This background noise can simply be subtracted out in the final analysis by, for example, performing a standard assay without the inclusion of the target polynucleotide sequence which triggers the cascade of multiple sequential displacement reactions. During the performance of the standard assay a base line can be determined which can later be used during data analysis for an actual assay using target polynucleotide sequences to normalize the data.

The polynucleotide sequences of the present invention are designed based upon two considerations. The first of these is the target polynucleotide sequence and secondly, the polynucleotide sequences that will comprise the components of the cascade that will facilitate multiple sequential displacement reactions.

Figure 1B:
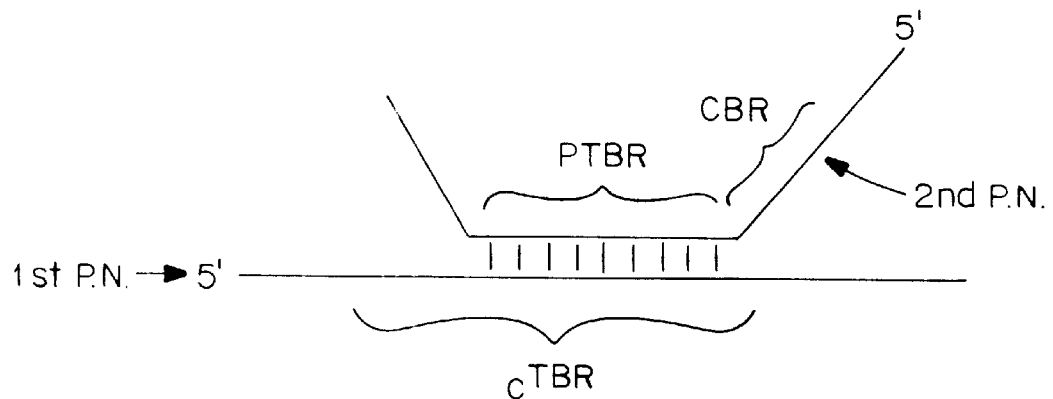
FIG. 1b is a schematic representation of the polynucleotides used in the present invention.
Figure 1C:
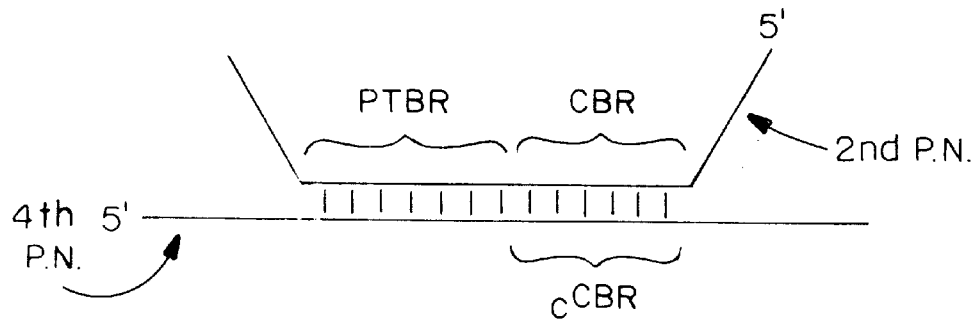
FIG. 1c is a schematic representation of the polynucleotides used in the present invention.

The target polynucleotide sequence has a region to which a designed polynucleotide sequence (referred to herein as the first polynucleotide sequence) will bind. This region is referred to herein as the "target binding region", or "TBR". (See FIG. 1). Preferably, this TBR is from about 5 to about 1000 nucleotides in length, more preferably 15 to about 200. Generally, the nucleotide sequence which comprises this region is known prior to the commencement of the assay. Based on this understanding of the TBR sequence, the first polynucleotide sequence can be designed and manufactured, for example, using a nucleic acid synthesizer. The region of the first polynucleotide sequence which binds to the TBR is referred to herein as CTBR, standing for the "complementary target binding region". (See FIG. 1). The CTBR will contain a nucleotide sequence that is complementary to the TBR. Preferably, the degree of complementarity between the CTBR and TBR is from about 95 to about 100% complementary to each other. The first polynucleotide sequence can contain cis nucleotide sequences outside the CTBR, wherein the CTBR is embedded within other nucleotide sequences of the first polynucleotide or is positioned at either the 5' or 3' end of the first polynucleotide.

The second polynucleotide sequence used in the present invention will be comprised of at least two regions. One region is a partial TBR, that is, it shares partial substantial identity with the TBR of the target polynucleotide (PTBR). (See FIG. 1). Preferably, this partial substantial identity is from about 95% to about 100% substantially identical to each other with respect to the TBR. The second region is a nucleotide sequence region that will interact with and hybridize to another polynucleotide sequence in the next probe complex. This second region, however, lacks complementarity with the first polynucleotide, precluding any interaction between this second region and the first polynucleotide. This second region is referred to herein as "Cascade Binding Region", or simply, "CBR". (See FIG. 1).

Figure 2:
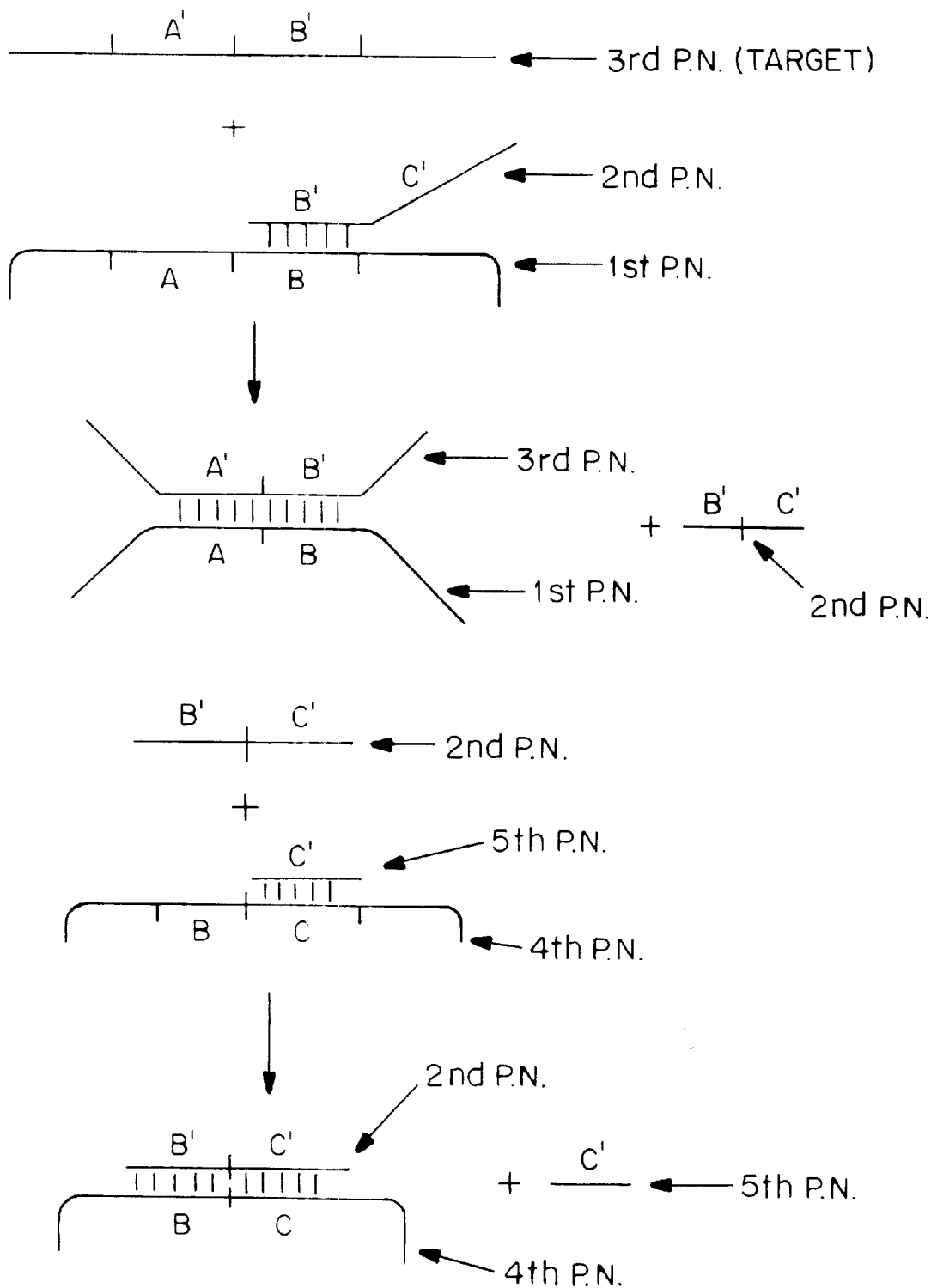
FIG. 2 is an illustration of sequential probe and displacement complex formation with the generation of displacement polynucleotide sequences.

The association between the CBR sequence of the second polynucleotide and the complementary region of the next probe complex (cCBR, FIG. 1c) causes the displacement of the fifth polynucleotide from its complex with the fourth polynucleotide. (See FIG. 2). Thus, the presence of CBR sequences in the displaceable polynucleotides allows for the propagation of a cascade of sequential displacement reactions involving multiple probe complexes. In general, each displaceable polynucleotide will have at least one CBR. In cases where gain of signal is produced at each displacement reaction, each displaceable polynucleotide will have multiple CBRs, wherein each CBR will cause displacement of a distinct displaceable polynucleotide in the next probe complex with which it is contacted. In preferred embodiments where gain of signal is desired, it is most convenient if the multiple CBRs are identical sequence repeats. This enables all displaced polynucleotides to react productively with a single type of probe complex in the subsequent displacement reaction.

The polynucleotide sequences of the present invention are constructed based upon designing partial or full hybridization partners in order to construct a multiple sequential displacement cascade through designing complementary CBRs. For illustrative purposes only, polynucleotide partners of a partial hybridization will share less complementary CBRs than polynucleotide partners in a full hybridization complex. Generally, the displaced polynucleotide sequence from a displacement complex will possess a complementary CBR(s) to constituent polynucleotide sequence in a subsequent displacement complex. Further, at least one partner of the complex will have a higher affinity for the displaced polynucleotide sequence based upon a higher degree of complementarity of CBRs between them, which is by design, hence there will be a displacement of a polynucleotide sequence having less complementarity. The displacement cycle continues until there are no displacement complexes that are susceptible to interaction with a previously displaced polynucleotide sequence. (See FIG. 1).

In a preferred embodiment, the probe complexes will have sufficient duplex stability to allow the procedure to be carried out at ambient temperature, approximately, 25° C.

Methods for determining the thermal stability of hybridization complexes are well known in the literature. Wetmur, *Critical Reviews in Biochemistry and Molecular Biology*, 26:227–259 (1991); Quartin and Wetmur, *Biochemistry*, 28:1040–1047 (1989). Application of these methods to estimation of displacement complex stability concerns the following reaction:

wherein D and D' are complementary polynucleotide sequences, B is the displacement complex product and $k_2$ and $k_r$ are the kinetic rate constants for the displacement complex formation and dissociation, respectively. In this scheme, the reverse reaction is most relevant to the consideration of spontaneous dissociation of the displacement complex, and the rate constant for dissociation, $k_r$, is the critical variable that needs to be minimized to reduce spontaneous background. For a given displacement complex, spontaneous dissociation can be reduced by lowering the assay temperature; this will decrease the dissociation constant.

Once a measurement of the dissociation constant has been obtained for one experimental temperature, the Arrhenius equation (2) can be rearranged to calculate the $k_r$ for other temperatures as follows:

$$k = A \exp(-Ea/RT) \tag{2}$$

$$k_{r1}/k_{r2} = \exp[(Ea/R)\{1/T_2) - (1/T_2)\}] \tag{3}$$

wherein $k_{r1}$ and $k_{r2}$ are the displacement complex dissociation rate constants at temperature $T_1$ and $T_2$, Ea is the activation energy for dissociation and R is the universal gas constant. The term Ea can be calculated from the base sequence of the polynucleotide sequence used to form the displacement complex. Wetmur, *Critical Reviews in Biochemistry and Molecular Biology*, 26:227–259 (1991). Use of the Arrhenius equation for this calculation is described by Tinocco, et al., Physical Chemistry: Principles and Applications in Biological Sciences, Prentice Hall (pub.), Englewood Cliffs, N.J., pp. 290–294 (1978).

In the case where the hybridization-displacement reactions occur in spatially separate regions of a solid support matrix, such a an electrophoresis matrix, an effective dissociation constant can be estimated using a temperature gradient procedure. See Example 2. The melting behavior of an immobilized displacement complex within an electrophoresis gel can be measured using a temperature gradient which increases laterally across the gel. The temperature, Td, at which 50% of the complex has dissociated during the time of electrophoresis, ta, can be used to estimate the dissociation constant.

Considering the dissociation as a first order reaction with kinetic rate constant $k_r$, it follows that at Td:

$$\ln(0.5) = -k_r ta \quad (4)$$

$$k_r = -0.693/ta \quad (5)$$

Thus, using temperature gradient gels allows for the measurement of an effective value for $k_r$, Td and ta. Once $k_r$ has been evaluated at Td, equation (3) can be used to calculate $k_r$ at other lower temperatures that might be suitable for the displacement assay. These calculated values of $k_r$ can then be used with the first order rate law to calculate the fraction of displacement complex remaining at a given assay temperature ta and electrophoresis time ta:

$$\ln(B/Bo) = -k_r ta \quad (6)$$

wherein B is the concentration of displacement complex remaining at time ta, and Bo is the initial concentration of the complex. Equation (6) can be used to estimate the change in $k_r$ needed to increase B/Bo (decrease displacement complex dissociation) by any specified amount. Once the desired value of $k_r$ is known, equation (3) can be used to calculate the change in temperature needed to achieve the $k_r$ value.

It should be noted that the gradient gel procedure only provides an estimate of the actual displacement complex Td and $k_r$, since displaced polynucleotides can re-hybridize to un-hybridized single-stranded immobilized polynucleotide sequences until they pass out of the displacement layer. In general, the experimentally determined values will overestimate the actual Td and underestimate the actual $k_r$ for the irreversible microscopic displacement complex dissociation reactions. Nevertheless, the quantitative relationships given in equations (1) through (6) provide a rational and practical framework for predicting the stability of displacement complexes, and design of multiple displacement protocols.

The displaced polynucleotide sequences of the methods, can be separated from a hybridization complex. For example, the displaced polynucleotide sequences can be separated based on the size difference between the displaced polynucleotide sequence and the complex. Generally, the displaced polynucleotide sequences generated by the methods herein consist of liberated polynucleotide sequences from displacement complexes. Size separation can be accomplished by size-exclusion chromatography, filtration, centrifugation, size-partitioning using size-sensitive membranes, migration through a solid support such as a polyacrylamide gel, starch gel, agarose gel, etc. One of ordinary skill in the art will be familiar with the various techniques of employing size separation that can be used in the present invention. Separation of the signal(s) from a complex may also be based upon the immobilization of the complex while having the signal(s) remain free in solution. If the hybridization complex is immobilized to a surface while the displaced polynucleotide sequence remains free in solution, this allows for the separation of the signal(s) from the complex by mechanical transfer, for example, using a pipette, or migration of the signal(s) by various means. Some of these means comprise migration through a matrix, such as a gel, and include, but are not limited to, electrophoresis, electrically-induced endosmotic flow, wetting, capillary action, and pumped liquid flow.

The detected signal(s), for example, generated from a displaced polynucleotide sequence during a displacement complex reaction, can be measured, recorded, plotted and processed by any practicable means. The quality of the detected signal, and its ability to be used for subsequent analysis, may be improved by any practicable techniques. A detected signal may be monitored and measured from before the commencement of the assay, or from any point therein. Methods of detecting a signal(s) include, but are not limited to, mass or density measurement, mass spectrometry, plasmon resonance, optical emission or absorption, fluorescence, phosphorescence, luminescence, chemiluminescence, polarization, refractive index changes, electrical conductivity, radioactivity, viscosity, turbidity and optical rotation. Examples of signals include, but are not limited to, radioactive isotopes attached to a polynucleotide sequence, an affinity reagent, such as biotin, attached to a polynucleotide sequence, or an intercalating fluorescent dye interacting with a polynucleotide sequence or hybridization complex. One of ordinary skill in the art will he familiar with these various techniques that can be used in the present invention.

The basic embodiment of the invention pertains to a method of detecting a target polynucleotide sequence in a biological sample. This method involves a sequential series of probe and displacement complex formation.

A first probe complex is formed by contacting a first polynucleotide sequence with a second polynucleotide sequence under conditions suitable that will facilitate chemical hybridization between the first and second polynucleotide sequence. Preferably, the first polynucleotide sequence has a high degree of complementarity, therefore high affinity, with the target polynucleotide sequence as compared to the second polynucleotide sequence range of 95–100%.

A first displacement complex is formed by contacting the first probe complex with a target polynucleotide sequence (referred to herein as target third polynucleotide sequence) under conditions suitable to facilitate the displacement by and hybridization of the target third polynucleotide sequence. Preferably, the first polynucleotide sequence of the complex has a higher affinity for the target third polynucleotide sequence than with its second polynucleotide sequence complex partner. Based on this affinity difference, the target polynucleotide sequence will compete off at least one second polynucleotide sequence from the first probe complex. A new complex results having the first and target polynucleotide sequences hybridized together via base-pairing, while the second polynucleotide sequence is displaced.

This probe and displacement complex cycle is followed by a second cycle of probe and displacement complex formation. The second probe complex is formed by contacting a fourth and fifth polynucleotide sequence under conditions suitable for hybridization. Preferably, the fourth polynucleotide sequence has a higher affinity for the displaced second polynucleotide sequence than for its fifth polynucleotide sequence complex partner. The second displacement complex is formed by contacting the second probe complex with the displaced second polynucleotide sequence which is the product of the first displacement reaction. Given that the fourth polynucleotide sequence has greater affinity for the displaced second polynucleotide sequence than for its fifth polynucleotide sequence partner, at least one fifth polynucleotide sequence will be competed off from the second probe complex by the displaced second polynucleotide sequence. As a result of this displacement event, a new complex will be formed between the fourth and second polynucleotide sequence leaving the fifth polynucleotide sequence free. This fifth polynucleotide sequence can now generate a signal which is subject to detection. For example, this fifth polynucleotide sequence can be embedded within a nucleic acid that is labeled with radioactive phosphate atoms that can be detected. Alternatively, if more cycles are contemplated, then this fifth polynucleotide sequence could serve as a displacing polynucleotide sequence in a subsequent displacement complex. By continuing the cycles, the amplification of the signal(s), is effectuated. Also, If multiple polynucleotide sequences are employed, for example, more than two fifth polynucleotide sequences used in complex formation, this multiplication will continue throughout the assay amplifying the assay signal.

Further cycles of probe complex and displacement complex formation are also envisaged in this embodiment which serve to amplify the signal(s) generated. Probe complexes are formed by successive polynucleotide sequences under conditions suitable for hybridization as articulated for the formation of the probe complexes above. Preferably, at least one member of the complex will have greater affinity for the displaced nucleotide, that was generated during a previous cycle of displacement, than for its current hybridization partner. The member of the complex that has a high affinity for the displaced polynucleotide sequence is referred to herein as the cognate polynucleotide sequence. A cognate polynucleotide sequence is that sequence which preferably is from about 95% to about 100% complementary to a second polynucleotide sequence and will hybridize to the second polynucleotide sequence under from about medium to about high stringency conditions which are well known to the art. This probe complex formation is then followed by a round of displacement complex formation. In this round, the probe complex just created is contacted by a displaced polynucleotide sequence that was generated in a previous cycle, preferably in the immediately preceding cycle. Preferably, at least one member of the complex has a higher affinity for the displaced polynucleotide sequence that for any constituent polynucleotide sequence in the complex. Based on affinity differences, the displaced polynucleotide sequence will displace a at least one polynucleotide sequence hybridized in the probe complex and hybridize to its cognate polynucleotide sequence forming a new complex. The new displaced polynucleotide sequence can then generate a signal which can be detected for the current assay (e.g, a detectably-labeled polynucleotide). (See FIG. 2).

Figure 3:
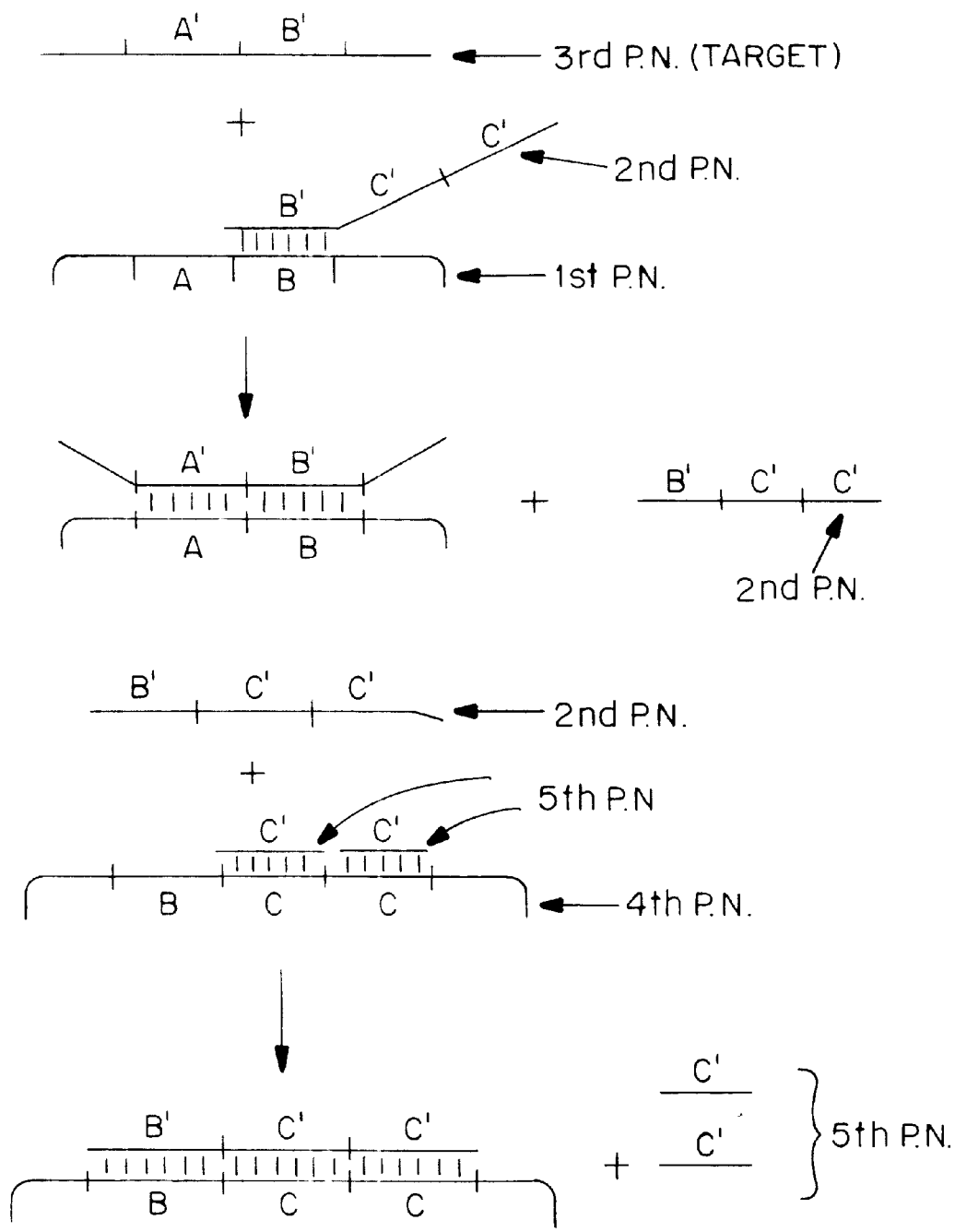
FIG. 3 is an illustration of sequential probe and displacement complex formation with amplification of the assay signal.

This embodiment also pertains to the use of multiple repeating units of polynucleotide sequences for amplifying the assay signal. In this aspect of the embodiment, the second and fourth polynucleotide sequences contain multiple repeating units of identical sequence per unit, wherein these repeating units are complementary as between the second and fourth polynucleotide sequence. The relationship between the second and fourth polynucleotide sequences is such that they could base pair with respect to their respective repeating units. The fifth polynucleotide sequence, or at least a portion of it is substantially identical (from about 95% to about 100%), to at least one repeat unit of the second polynucleotide sequence. As the assay reaction cycles progress from the first probe complex, multiple fifth polynucleotide sequences will be generated per target polynucleotide sequence assayed and hence multiple signals will be generated. (See FIG. 3).

Additionally, this embodiment embraces performing this assay in parallel. One set of conditions would include the putative target polynucleotide sequence, whereas a paralleled assay would be performed without employing a target polynucleotide sequence. In this second, or paralleled, assay all other components of the assay would remain the same. The signal detected for the assay without the target polynucleotide sequence can represent background or noise. This noise can be used to normalize the signal response obtained from the assay which included a target polynucleotide sequence.

In another embodiment of the invention, a method for detecting a target polynucleotide sequence in a nucleic acid molecule within a sample using a recursive cycle comprising multiple sequential polynucleotide displacement is disclosed. In this particular embodiment, cycles of probe complex and displacement complex formation occur in which complex reactants are generated that allow for the recycling of the assay, thereby generating multiple signals.

A first probe forming complex is generated by contacting a first polynucleotide sequence with a second polynucleotide sequence under conditions suitable for hybridization. Preferably, the first polynucleotide sequence has a higher degree of affinity for the target third polynucleotide sequence as compared to its second polynucleotide sequence complex partner. A first displacement complex is formed by contacting the first probe complex with a target third polynucleotide sequence. This target polynucleotide sequence will displace the second polynucleotide sequence and hybridize to the first polynucleotide sequence due to the affinity between the target and first polynucleotide sequences. The second polynucleotide sequence will be displaced and remain free of the complex now formed between the first and target polynucleotide sequences.

This probe and displacement complex cycle is followed by a second cycle of probe and displacement complex formation. The second probe complex is formed by contacting a fourth and fifth polynucleotide sequence under conditions suitable for hybridization. Preferably, the fourth polynucleotide sequence has a higher affinity for the displaced second polynucleotide sequence than for its fifth polynucleotide sequence complex partner. Preferably, the fifth polynucleotide sequence is partially identical (from about 30% to about 95%) to the target polynucleotide sequence. The second displacement complex is formed by contacting the second probe complex with the displaced second polynucleotide sequence which is a product of the first displacement complex. Given that the fourth polynucleotide sequence has greater affinity for the displaced second polynucleotide sequence than for its fifth polynucleotide sequence partner, at least one fifth polynucleotide sequence will be competed off from the second probe complex by the displaced second polynucleotide sequence. As a result of this displacement event, a new complex will be formed as between the fourth and second polynucleotide sequence leaving the fifth polynucleotide sequence free. This fifth polynucleotide sequence can now generate a signal which is now subject to detection. For example, this fifth polynucleotide sequence can be embedded within a nucleic acid that is labeled with radioactive phosphate atoms that can bc detected. Alternatively, this fifth polynucleotide sequence can serve as a displacing polynucleotide sequence in the next displacement complex.

A third probe complex is formed by contacting a sixth polynucleotide sequence with a seventh polynucleotide sequence under conditions suitable in an aqueous medium for hybridization between the sixth and seventh polynucleotide sequences. Preferably, the degree of homology between the seventh polynucleotide sequence and the target polynucleotide sequence is from about 95% to about 100%. Most preferably, the seventh polynucleotide sequence is the target third polynucleotide sequence. The sixth polynucleotide sequence preferably has a higher affinity for the displaced fifth polynucleotide sequence than for its hybridization partner.

Figure 4:
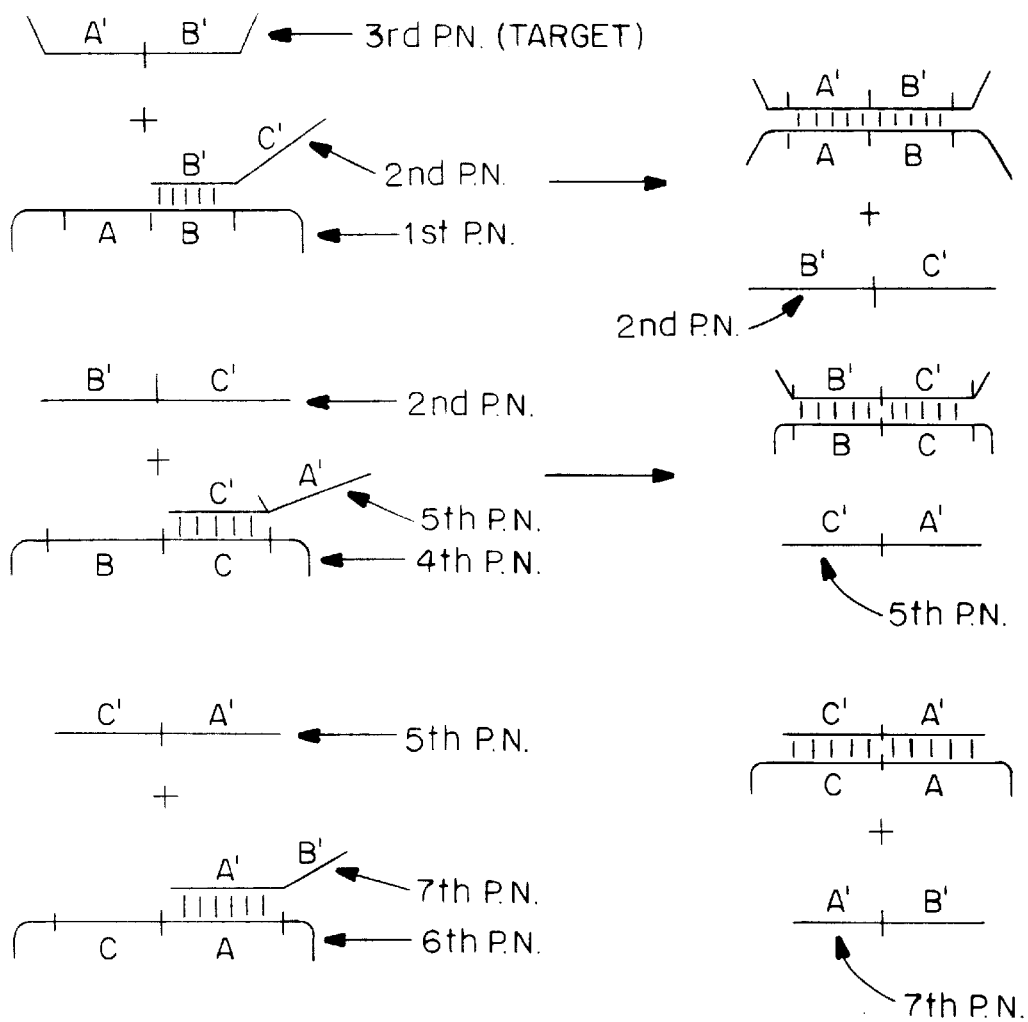
FIG. 4 is an illustration of a recursive cycle using sequential probe and displacement complex formation with the generation of the target polynucleotide sequence.

A third displacement complex is formed by contacting the third probe complex with the displaced fifth polynucleotide sequence under conditions suitable for the displacement of at least one seventh polynucleotide sequence from the probe complex and the hybridization to the sixth polynucleotide sequence by the fifth polynucleotide sequence. The (displaced seventh polynucleotide sequence can now be cycled back to the first displacement complex, thereby initiating the entire sequence of cycles again. This generation of seventh polynucleotide sequences, as well as any other multiple displaced polynucleotide sequences, can serve to generate signals. (See FIG. 4).

Figure 5:
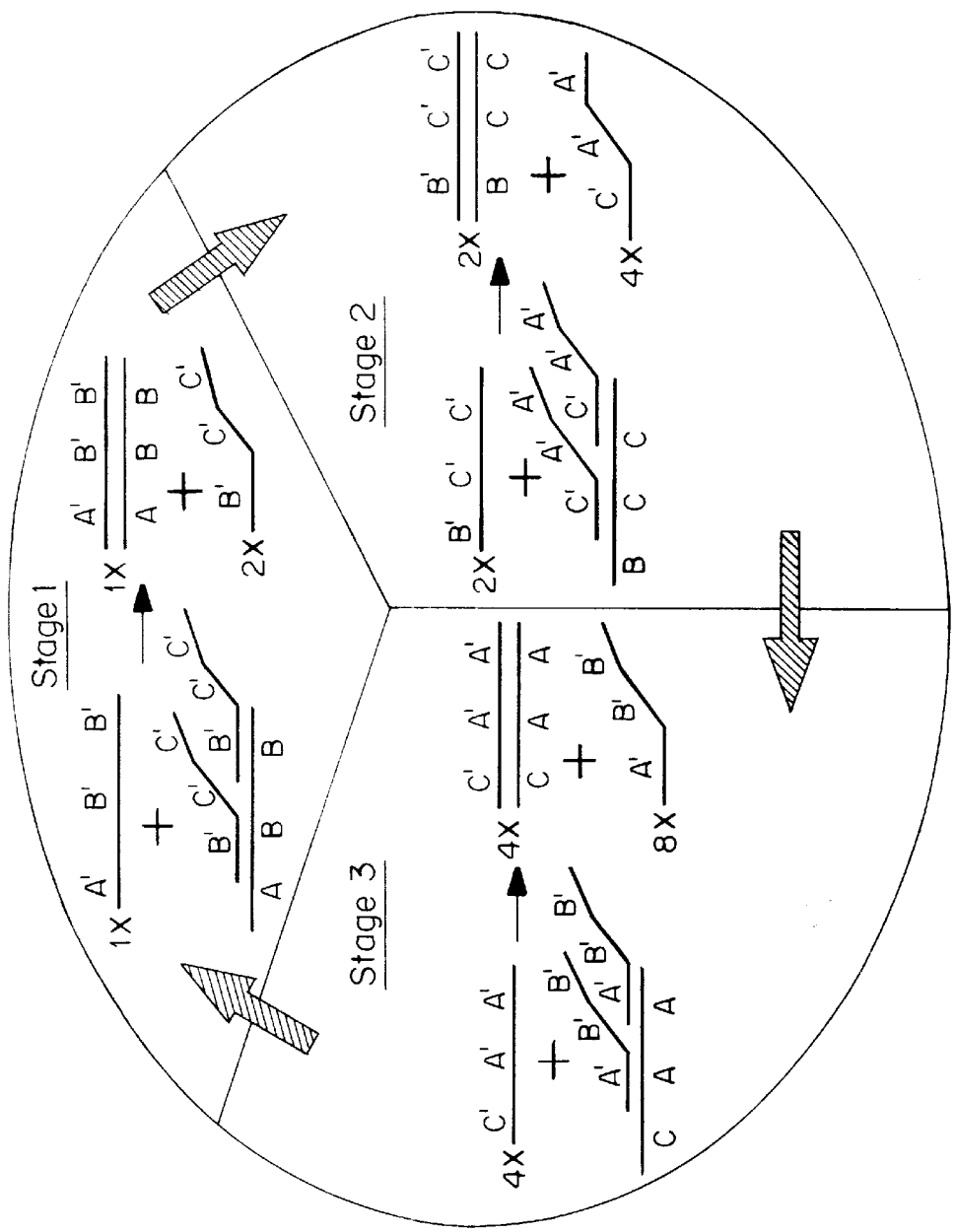
FIG. 5 is an illustration of a recursive cycle with gain or amplification of the assay signal using sequential probe and displacement complex formation with the generation of the target polynucleotide sequence.

A recursive cascade of displacement reactions with gain of signal at each individual displacement reation can be used to achieve high levels of amplification as illustrated in FIG. 5. The probe complexes illustrated are designed to provide a two-fold gain of signal for each displacement reaction. The multiplication factors in FIG. 5 indicate the stoichiometry of each individual displacement reaction in this embodiment. The total amplification achieved by a single cycle of three displacements with two-told gain of signal at each step is eight-fold. Each additional cycle of three displacements will further increase signal by eight-fold.

In another embodiment of the invention, a method for detecting a target polynucleotide sequence in a nucleic acid molecule within a biological sample using heterogenous polynucleotide sequences to generate multiple signals, comprising multiple sequential polynucleotide displacement for signal amplification is disclosed. In this embodiment, cycles of probe and displacement complex formation occur in which a bifurcation event takes place resulting in the production of multiple and distinct cycles, thereby generating multiple signals.

A first probe forming complex is generated by contacting a first polynucleotide sequence with a second polynucleotide sequence under conditions suitable for hybridization. Preferably, the first polynucleotide sequence has a higher degree of affinity for the target third polynucleotide sequence than with the second polynucleotide sequence. A first displacement complex is formed by contacting the first probe complex with a target third polynucleotide sequence. This target polynucleotide sequence will displace at lease one second polynucleotide sequence and hybridize to the first polynucleotide sequence due to the affinity between the target and first polynucleotide sequences. The second polynucleotide sequence will be displaced and remain free of the complex now formed between the first and target polynucleotide sequences.

A heterogenous probe complex is formed by contacting a fourth polynucleotide sequence with a fifth and sixth polynucleotide sequence under conditions suitable for hybridization between the fourth with the fifth and sixth polynucleotide sequences, or as many as are being employed in the assay. The fifth and sixth polynucleotide sequences are sufficiently different (i.e., that they cannot hybridize to each other's complements under conditions of the assay) from one another so as to be called heterogenous polynucleotide sequences, however, they both are capable of binding with the fourth polynucleotide sequence via base-pairing using different sites along the fourth polynucleotide sequence.

Figure 6:
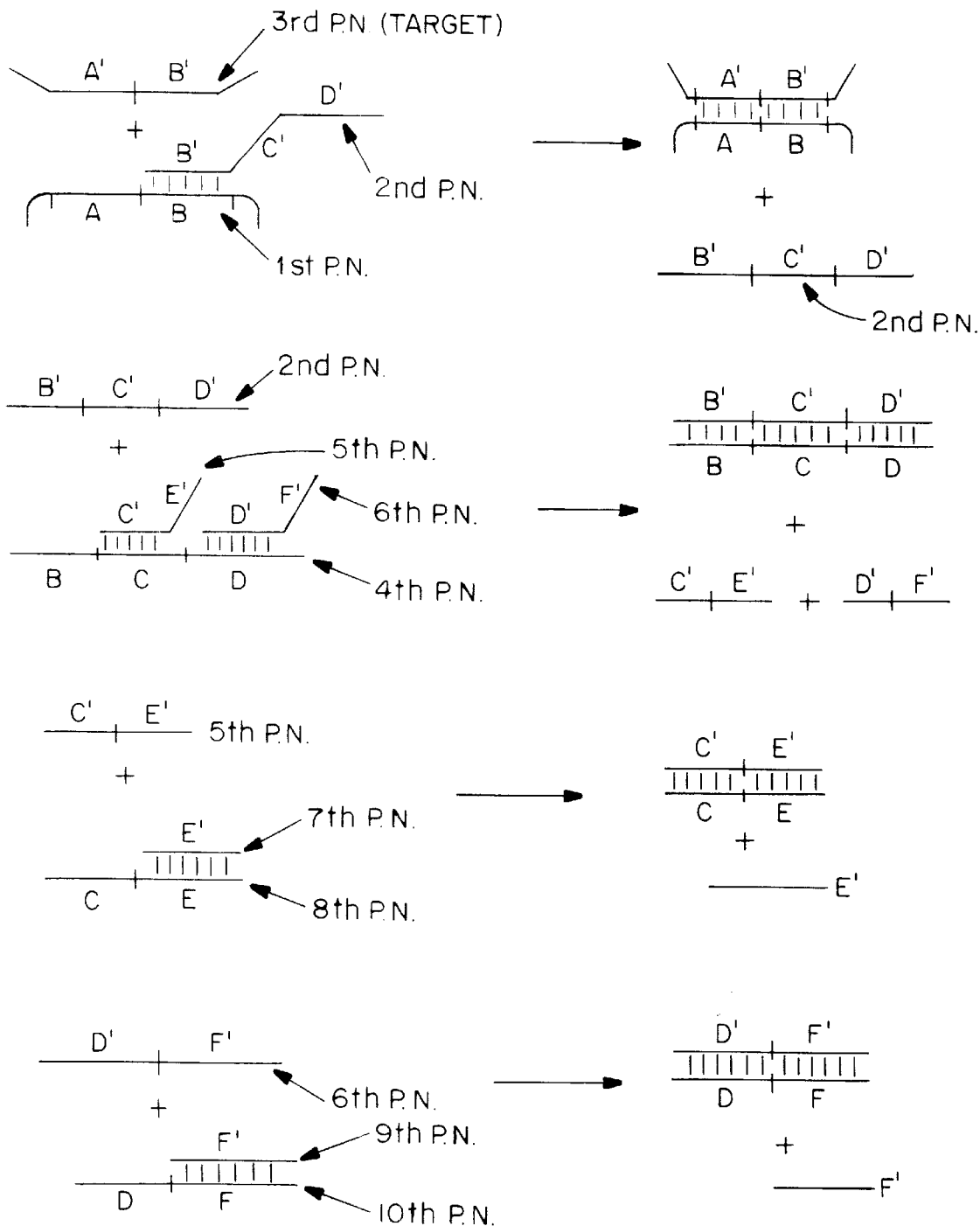
FIG. 6 is an illustration of sequential probe and displacement complex formation generating heterogenous assay signals.

A heterogeneous displacement complex is formed by contacting the displaced product from the previous displacement complex event, in this case, the displaced second polynucleotide sequence, with the heterogeneous probe complex under conditions suitable for displacement and hybridization. Preferably, the second polynucleotide sequences will displace at least one fifth and at least one sixth polynucleotide sequence (and any other polynucleotide sequence that is hybridized to the fourth polynucleotide sequence) and hybridize to the fourth polynucleotide sequence. The displacement and hybridization events are based upon the fourth polynucleotide sequence having a higher affinity for the second polynucleotide sequence than any other polynucleotide sequence present. This last event in the heterogeneous probe and displacement complex cycle generates at least two signals from the fifth and sixth polynucleotide sequences. The number of different potential signals generated depends upon how many species of non-substantially identical polynucleotide sequences are used to hybridize with the fourth polynucleotide sequence during the heterogeneous probe formation step. By non-substantially identical it is meant herein that the different polynucleotide sequences will not hybridize with any of the other polynucleotide sequences present, including the fourth polynucleotide sequence under the conditions of the assay. However, the polynucleotide sequence(s) used to hybridize with the fourth polynucleotide sequence can be fully or partially substantially identical to the target third polynucleotide sequence. (See FIG. 6).

Further amplification of the assay signals can be generated by forming further multiple probe complexes. The new probe complexes utilize the cognate polynucleotide sequences of the displaced polynucleotide sequences generated from the heterogenous displacement complex. These complexes are formed by contacting cognate polynucleotide sequences with polynucleotide sequences that are partially complementary to their respective cognate polynucleotide sequence under conditions suitable for hybridization.

Multiple displacement complexes are then formed. These complexes are created by contacting the multiple probe complexes with displaced polynucleotide sequences (which were generated during the previous heterogeneous displacement complex event) under conditions suitable for displacement and hybridization. The cognate polynucleotide sequences will bind to their respective complementary displaced polynucleotide sequences, and based upon the affinity between them, the hybridization partners of the cognate polynucleotide sequences will be displaced from the complex. The newly displaced polynucleotide sequences can now generate at least one signal which is subjected to detection. (See FIG. 6).

The present invention pertains to a method of detecting two or more heterogenous target polynucleotide sequences in a biological sample using a homogenous signal which can be detected, comprising multiple sequential polynucleotide displacement for signal amplification.

The formation of first heterogeneous probe complexes occurs by contacting a set of heterogeneous first polynucleotide sequences with a set of heterogeneous second polynucleotide sequences under conditions suitable for hybridization. Preferably, the heterogenous first polynucleotide sequences are full or partial complementary sequences to their respective target third polynucleotide sequence. The term heterogeneous is used to indicate that the population of probe complexes formed is a mixture of different first polynucleotide sequences hybridized to their complex partner; also, that the second polynucleotide sequences are also diverse and therefore contribute to the heterogeneity of the probe complex. The first and second polynucleotide sequences are determined based upon the heterogenous population of target third polynucleotide sequences which are the subject of the assay. All of the second polynucleotide sequences share at least one common polynucleotide sequence region (hereinafter referred to as, "CNSR") that does not bind, due to lack of complementarity, to a first or third polynucleotide sequence. These CNSRs can be distinct from CBRs. in a more preferred embodiment, all of the second polynucleotide sequences have at least two CNSRs, that is, CNSR(1) and CNSR(2).

The formation of first heterogeneous displacement complexes occurs by contacting the first heterogenous probe complexes with their respective target third polynucleotide sequence (for every heterogenous probe complex formed there is a corresponding target polynucleotide sequence) under conditions suitable for the target third polynucleotide sequence to displace at least one second polynucleotide sequence and hybridize to its cognate first polynucleotide sequence, based upon affinity differences. Preferably, the first polynucleotide sequence of a complex will have greater affinity for its respective target third polynucleotide sequence. This reaction is repeated for all of the target third polynucleotide sequences subject to analysis. The term heterogeneous is used in this case to indicate that the population of displacement complexes formed is a mixed group formed from the heterogenous probe complexes. These displacement complexes generate a diverse population of displaced second polynucleotide sequences.

A second probe complex is formed by contacting a fourth polynucleotide sequence with a fifth polynucleotide sequence under conditions suitable for hybridization between the fourth and fifth polynucleotide sequence. In a preferred embodiment, the fifth polynucleotide sequence has a region which is substantially identical to the CNSR of the second polynucleotide sequences. Preferably, the fourth polynucleotide sequence has at least two CNSR complementary regions, one of which will interact with the fifth polynucleotide sequence's CNSR. Most preferably, the fifth polynucleotide sequence has a region that is substantially identical to only one CNSR of the second polynucleotide sequence which can be used to bind with the fourth polynucleotide sequence. Preferably, the fifth polynucleotide sequence binds to the fourth nucleotide via this CNSR.

Figure 7:
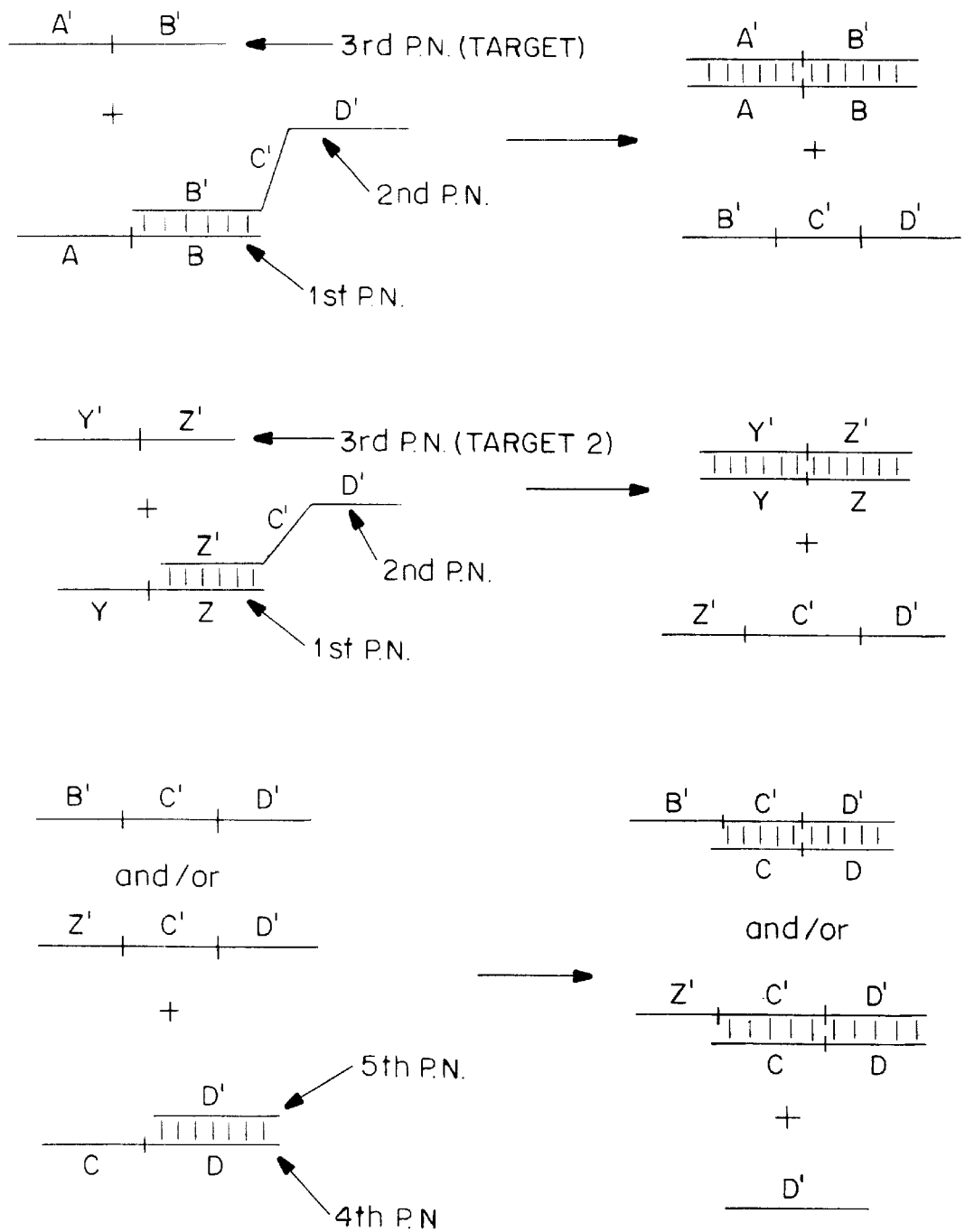
FIG. 7 is an illustration of the analysis a set of multiple heterogenous target polynucleotide sequences using sequential probe and displacement complex formation generating a homogenous assay signal.

A second displacement complex is formed by contacting the displaced second polynucleotide sequences, generated from the first heterogeneous displacement complexes, with the second probe complex under conditions suitable for (i) the displacement of at Least one fifth polynucleotide sequence from the second probe complex by the second polynucleotide sequence; and, (ii) the hybridization of the second polynucleotide sequence to the fourth polynucleotide sequence of the second probe complex. Preferably, this hybridization of the second polynucleotide sequence with the fourth polynucleotide sequence is through at least both CNSRs. As a result, at least one fifth polynucleotide sequence is displaced and free from the complex, therefore, it can generate a homogenous assay signal for the diverse population of target polynucleotide sequences analyzed. (See FIG. 7).

The present invention pertains to a method for detecting a target polynucleotide sequence in a nucleic acid molecule within a biological sample using an immobilized probe comprising multiple sequential polynucleotide displacement for signal amplification.

An immobilized probe complex is formed by contacting a first polynucleotide sequence with a second polynucleotide sequence under conditions suitable for hybridization between the first and second polynucleotide sequence. See U.S. Ser. Nos. 08/971,845; 06/016,708; and 08/812,105; the entire teachings of which are incorporated by reference. The first polynucleotide sequence is immobilized to a first surface. The surface of the present invention can be a surface on a solid support, such as, gels (like, polyacrylamide, starch or agarose), glass, plastic and wax-based.

The means of attachment of a nucleic acid to a surface, such as a solid support surface, can be by simple adsorption. Preferably, the attachment is mediated through a covalent bond between the nucleic acid and some chemical moiety associated with the surface, for example, an amine or carboxyl group, or acrylamide bound to any region of the nucleic acid. Chemical crosslinkers can be employed to immobilize a nucleic acid to a surface. An example of such a chemical crosslinker is carbodiimide (such as, 1-ethyl-3, 3-dimethylaminopropylcarbodiimide) which can be used to link the phosphate group on the 5' end of a nucleic acid with amine group on the surface. Additionally, ionic interactions can also facilitate such immobilization of the nucleic acid. The binding can be direct as between the nucleic acid and surface, or indirect such that an intermediate molecule lies between the nucleic acid and the surface. This intermediate molecule need not have any precise length.

Affinity reagents can also be employed as a means to immobilize a nucleic acid to a surface. For example, a nucleic acid carrying avidin or biotin moieties to a surface containing biotin or avidin moieties, respectively, will bind the nucleic acid to the surface. Another example of using an affinity-based immobilization technique is to coextensively link the nucleic acid of interest to an affinity ligand, again avidin or biotin provide useful examples. The cognate receptor to the ligand, for example, if biotin is the ligand, then avidin will be the cognate receptor, will have attached to it a magnetic particle. When a magnetic field is applied to the surface, the magnetic particle, along with that which attached to it, will be immobilized to the surface.

A displacement complex is formed by contacting the immobilized probe complex with a target third polynucleotide sequence under conditions suitable for the target polynucleotide sequence to displace at least one second polynucleotide sequence from the immobilized complex, and hybridize the target polynucleotide sequence with its cognate first polynucleotide sequence of the complex. Preferably, the first polynucleotide sequence has a higher affinity for the target third polynucleotide sequence than for the second polynucleotide sequence.

At least one displaced second polynucleotide sequence is transferred from the first immobilizing surface to a second immobilizing surface. The phase containing the displaced second polynucleotide sequence (or any displaced polynucleotide sequence), for example, a liquid phase, can be separated from an immobilized complex by processes such as chromatography, filtration, centrifugation, decantation or pipetting, for example. Additionally, transfer can be accomplished by counter current distribution, gravitational flow, electrically induced endosmotic flow, wetting, capillary action, pump-mediated flow and electrophoresis.

A second immobilized probe complex is formed by contacting a fourth polynucleotide sequence with a fifth polynucleotide sequence under conditions suitable for hybridization between the fourth and fifth polynucleotide sequences. The fourth polynucleotide sequence is immobilized to a second surface.

A second immobilized displacement complex is formed. The immobilized second probe complex is contacted with the transferred second polynucleotide sequence that was displaced during the first displacement complex event, under conditions suitable for the second polynucleotide sequence to displace at least one fifth polynucleotide sequence and hybridize to its cognate fourth polynucleotide sequence. Preferably, the fourth polynucleotide sequence has a higher affinity for the second polynucleotide sequence than for its fifth polynucleotide sequence complex partner. This second displacement complex event generates a fifth polynucleotide sequence that can be transferred to a subsequent surface or be used to generate a signal for detection.

Figure 8:
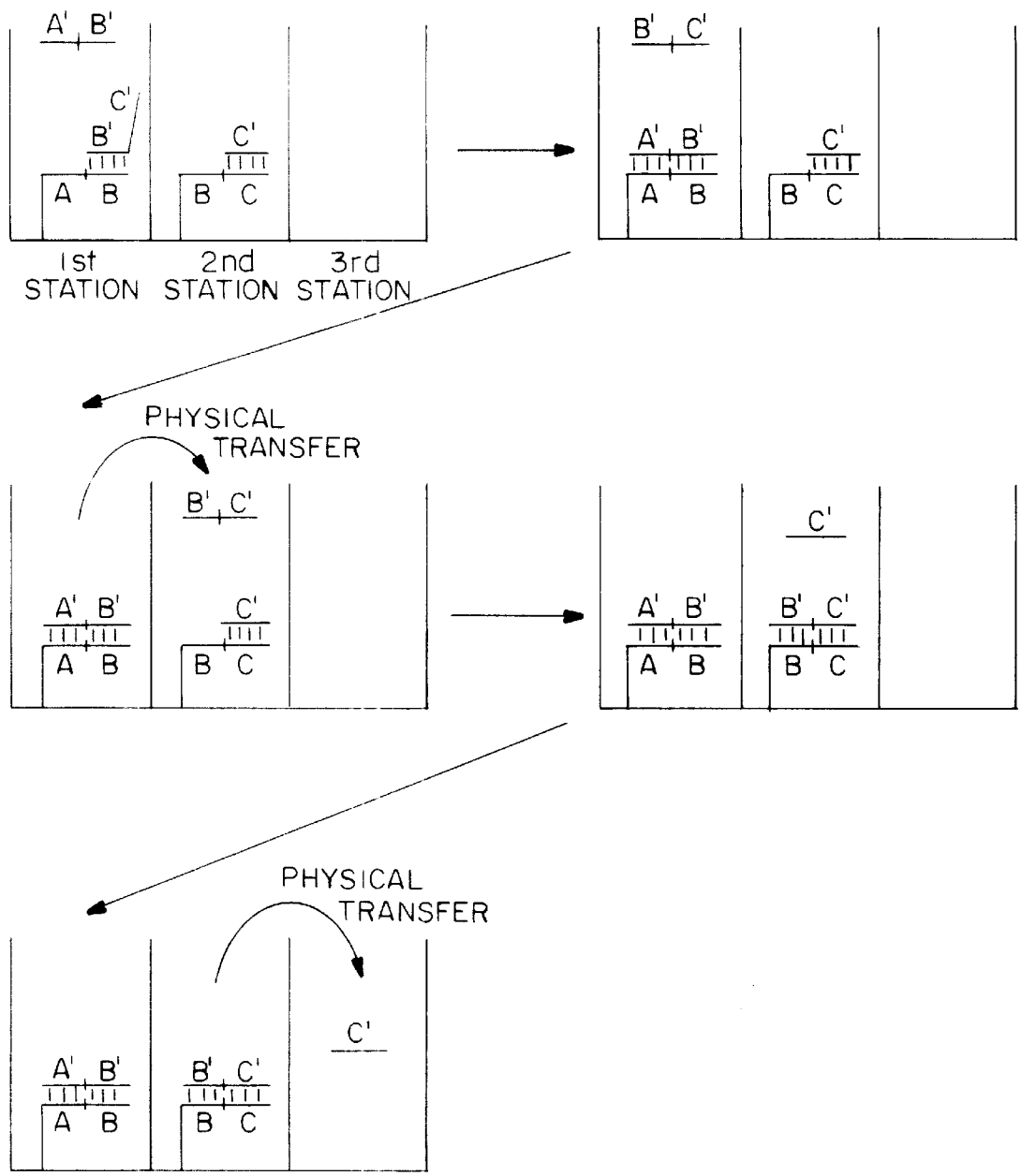
FIG. 8 is a schematic representation of multiple sequential displacement reactions using an immobilized polynucleotide sequence.

The cycle of probe and displacement complex formation followed by the transfer of the displaced polynucleotide sequence can be repeated with the result of amplifying the assay signal. Multiple cycles can involve multiple surfaces. These surfaces can be coextensive or spatially apart from one another, for example, two 50 mL conical tubes as representing two surfaces spatially apart. If the surfaces are coextensive they can be separated by partitions, for example, a size-selective permeable membrane which can separate coextensive surfaces allowing for only the movement of a displaced polynucleotide sequence containing molecule while retention of a complex (presumably not immobilized) in a particular surface is accomplished. (See FIG. 8).

Figure 9:
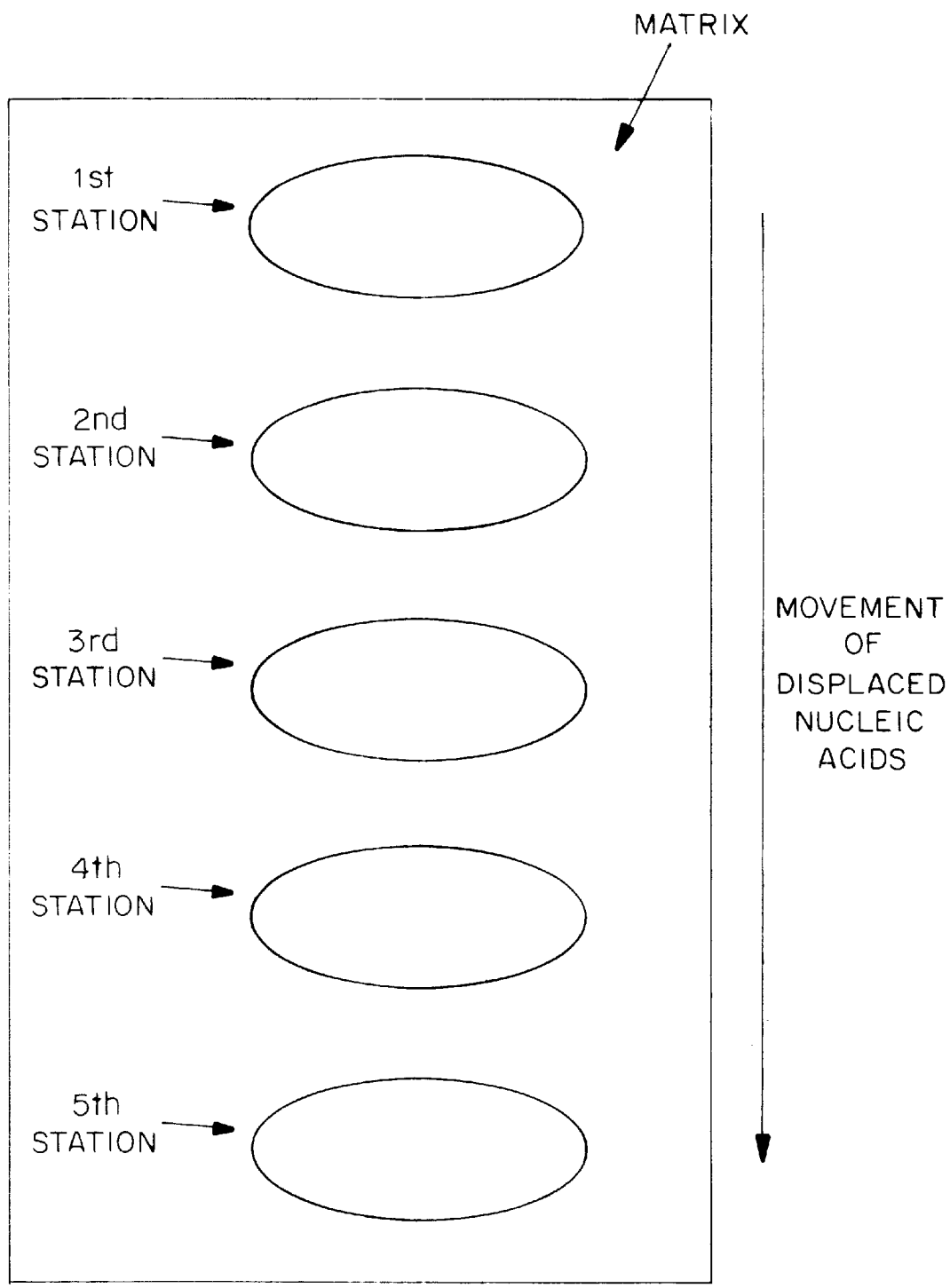
FIG. 9 is a schematic representation of multiple sequential displacement reactions using a solid support matrix, such as a gel.

This embodiment also embraces a solid support matrix wherein there are multiple reaction stations spatially aligned throughout the matrix; also, there need not be an immobilization of any complex. (See FIG. 9). These reaction stations are aligned along a matrix that has pockets within the matrix itself, such that reactants may be added to and confined in these pockets, thereby forming reaction stations. Probe complex and displacement complex formation can occur in these stations. These complexes can be physically separated by being in different reaction stations. The transfer from one station to the next can occur by mechanical transfer using, for example, a pipette. Transfer can also occur through the matrix, for example, by gravitational flow, electrically induced endosmotic flow, wetting, capillary action, pump flow and electrically induced electrophoretic flow. The support matrix itself can be a chromatographic support in the form of beads or particles, thin-layer plates, membranes, polyacrylamide gels, starch gels, agarose gels and other polymeric gels.

The multiple sequential polynucleotide displacement reactions described herein can be used as diagnostic methods for example, to detect the presence of, or absence of, polynucleotide sequences representative of bacteria, viruses, fungi and plant material in a biological. For any polynucleotide of known nucleotide sequence, polynucleotide probes can be designed as described herein. Using the methods described herein, one, or more polynucleotides representative of pathogenic or contaminating biological material can be detected. For example, to detect the presence of the human immunodeficiency virus (HIV) in a blood sample, polynucleotides can be designed as described herein that are complementary to and will hybridize with a polynucleotide sequence representative of HIV, thus detecting the presence of HIV in the biological test sample. The biological test sample can be used directly in the methods described herein or "prepared" for assay using methods well known to those of skill in the art (e.g., lysing cells to obtain the DNA or RNA present in the test sample or filtering or centrifuging the test sample). Another example is where it is desirable to detect a specific mutated region in the genome of an individual (or animal or plant). Some genetic mutations occur due to the insertion of nucleotide sequence into a host's genome. Polynucleotides can be designed as described herein that are complementary to and will hybridize to a nucleotide sequence representative of an insertion sequence, thus detecting the insertion sequence within the host's genome. One of ordinary skill in the art will be familiar with preparing a biological test sample for such an analysis.

The present invention further pertains to a diagnostic kit used for determining the presence or absence of a target polynucleotide sequence within a biological sample.

The kit comprises a first probe complex and a second probe complex. The first probe complex comprises a first polynucleotide sequence comprising a sequence complementary to a target polynucleotide sequence, hybridized to a second polynucleotide sequence. The second probe complex comprises a third polynucleotide sequence, comprising a sequence complementary to the second polynucleotide sequence of the first probe complex, hybridized to a labeled fourth polynucleotide sequence.

A first displacement complex is formed by contacting the first probe complex with a target third polynucleotide sequence. This target polynucleotide sequence will displace at least one second polynucleotide sequence and hybridize to the first polynucleotide sequence due to the affinity between the target and first polynucleotide sequences. The second polynucleotide sequence will be displaced and remain free of the complex now formed between the first and target polynucleotide sequences.

This displacement complex is followed by a second displacement complex formation. The second displacement complex is formed by contacting the second probe complex with the displaced second polynucleotide sequence which is a product of the first displacement reaction. Given that the third polynucleotide sequence has greater affinity for the displaced second polynucleotide sequence than for its fourth polynucleotide sequence partner, at least one fourth polynucleotide sequence will be competed off from the second probe complex by the displaced second polynucleotide sequence. As a result of this displacement event, a new complex will be formed as between the third and second polynucleotide sequence leaving the labeled fourth polynucleotide sequence free. This labeled fourth polynucleotide sequence is now subject to detection.

The label used can be radioactive, for example, a radioactive phosphorous atom. The label can also be a fluorescence label such as rhodamine. Alternatively, an affinity reagent, such as biotin covalently linked to the fourth polynucleotide sequence in any region of the polynucleotide. One of ordinary skill in the art will be familiar with these as well as other labels.

The features and other details of the invention will now be more particularly described and pointed out in the examples. It will be understood that the particular embodiments of the invention are shown by way of illustration and not as limitations of the invention. The principle features of this invention can be employed in various embodiments without departing from the scope of the invention.

EXAMPLES

Example 1

Signal Amplification by Multiple Sequential Displacement Reactions

Six 60-mer polynucleotide sequences were designed and synthesized. Each polynucleotide sequence has a tripartite structure forming a concatemer of three 20 nucleotide sequence motifs. The sequence motifs in the present example are designated D, E, F, cD, cE and cF, wherein "cX" refers to the sequence that is complementary to "X". See Table 1. Three of the six 60-mers (designated as "Ac" representing 5'-acrylamide modification of the polynucleotide sequence) were synthesized with 5'-acrylamide modifications to allow for immobilization of the polynucleotide sequence within polyacrylamide gels by copolymerization with an acrylamide monomer. The 5'-acrylamide modifications were added during automated synthesis using an acrylamide phosphoramidite (Acrydite™ phosphoramidite, Mosaic Technologies, Boston, Mass.). Immobilizable polynucleotide sequences and complementary displacement (or signal) polynucleotide sequences were hybridized in solution. These displacement polynucleotide sequences when displaced will serve as ultimately displace the signal polynucleotide sequence (E-CY3) which can be detected and is indicative of at least one sample target polynucleotide sequence. The signal polynucleotide sequence is labeled using CY3.

TABLE 1

| SEQ. ID. NO. | Polynucleotide sequence ID | Sequence |
| --- | --- | --- |
| 1 | D | 5'GTGCGGAAGGAGTGATGTAA |
| 2 | E | 5'CAAAAACGATAAACCAACCA |
| 3 | F | 5'AATGGAGAAAGACGGAGAGC |
| 4 | cD | 5'TTACATCACTCCTTCCGCAC |
| 5 | cE | 5'TGGTTGGTTTATCGTTTTTG |
| 6 | cF | 5'GCTCTCCGTCTTTCTCCATT |

The displacement (or signal) polynucleotide sequences were present in a 4-fold excess in concentration during the hybridization reaction to ensure saturation of all available complementary sites contained within the sequence of the immobilizable polynucleotide sequence. These polynucleotide sequence hybrids were then copolymerized into layers in a polyacrylamide slab gel by pouring each copolymer separately into individual slots. The arrangement of the immobilized displacement complexes is shown in FIG. 8a. The polynucleotide sequences used in this example are listed in Table 2.

TABLE 2

| Fluorescent signal polynucleotide sequence | |
| --- | --- |
| SEQ. ID. NO. 7; E-CY3 | 5'-CY3-CAAAAACGATAAACCAACCA-3' |
| Displacement polynucleotide sequences | |
| SEQ. ID. NO. 8; FDD | 5'AATGGAGAAAGACGGAGAGCGTGCGG AAGGAGTGATGTAAGTGCGGAAGGAGTG ATGTAA-3' |
| SEQ. ID. NO. 9; DEE | 5'GTGCGGAAGGAGTGATGTAACAAAAA CGATAAACCAACCACAAAAACGATAAAC CAACCA-3' |
| SEQ. ID. NO. 10; EFF | 5'CAAAAACGATAAACCAACCAAATGGA GAAAGACGGAGAGAGCAATGGAGAAAGA CGGAGAGC-3' |
| Immobilized polynucleotide sequence | |
| SEQ. ID. NO. 11; cEcEcD-Ac | 5'acrylamideTGGTTGGTTTATCGTT TTTGTGGTTGGTTTATCGTTTTTGTTAC ATCACTCCTTCCGCAC-3' |
| SEQ. ID. NO. 12; cFcFcE-Ac | 5'acrylamideGCTCTCCGTCTTTCTC CATTGCTCTCCGTCTTTCTCCATTCAAA AACGATAAACCAACCA-3' |
| SEQ. ID. NO. 13; cDcDcF-Ac | 5'acrylamideTTACATCACTCCTTCC GCACTTACATCACTCCTTCCGCACGCTC TCCGTCTTTCTCCATT-3' |

Hybridization was carried out using 2 µM immobilizable polynucleotide sequence and 8 µM displacement (or signal) polynucleotide sequence in 2×TBE (1×TBE is 89 mM Tris-borate, pH 8.3, 2 mM EDTA). The hybridization reactions were brought to 90° C. and slowly cooled to 40° C., at which temperature the hybridization reactions were performed for an additional 2 hours. Following hybridization, the polynucleotide sequence mixture was mixed 1:1 with 24% acrylamide dissolved in water. Ammonium persulfate and TEMED were added to 0.1% wt/vol and 0.1% vol/vol, respectively. The mixture was poured into horizontal slots (approximately 5 mm wide by 0.8 mm thick) within a precast 12%, 1×TBE polyacrylamide gel for polymerization.

After polymerization of the displacement layers, the gel was subjected to electrophoresis overnight at approximately 2–5 V/cm field gradient in the direction parallel to the long axis of the layers which will serve to remove non-immobilized excess signal and displacement polynucleotide sequences as well as non-immobilized displacement complexes. Following this step, the gel was re-orientated in the apparatus so that samples could be loaded perpendicular to the long axis of the layers and underwent electrophoresis through them sequentially.

The gel contained two probe layers amplification (layer 1 and 2), a probe for generating of a labeled displaced polynucleotide layer (layer 3) and a capture layer to concentrate the labeled displaced polynucleotide into a concentrated band (layer 4). (see FIG. 10a). Two pmoles of each of the three different model target polynucleotide sequences, EFF, FDD and DEE, were then loaded into separate lanes of the gel and were subjected to electrophoresis.

Figure 10A:
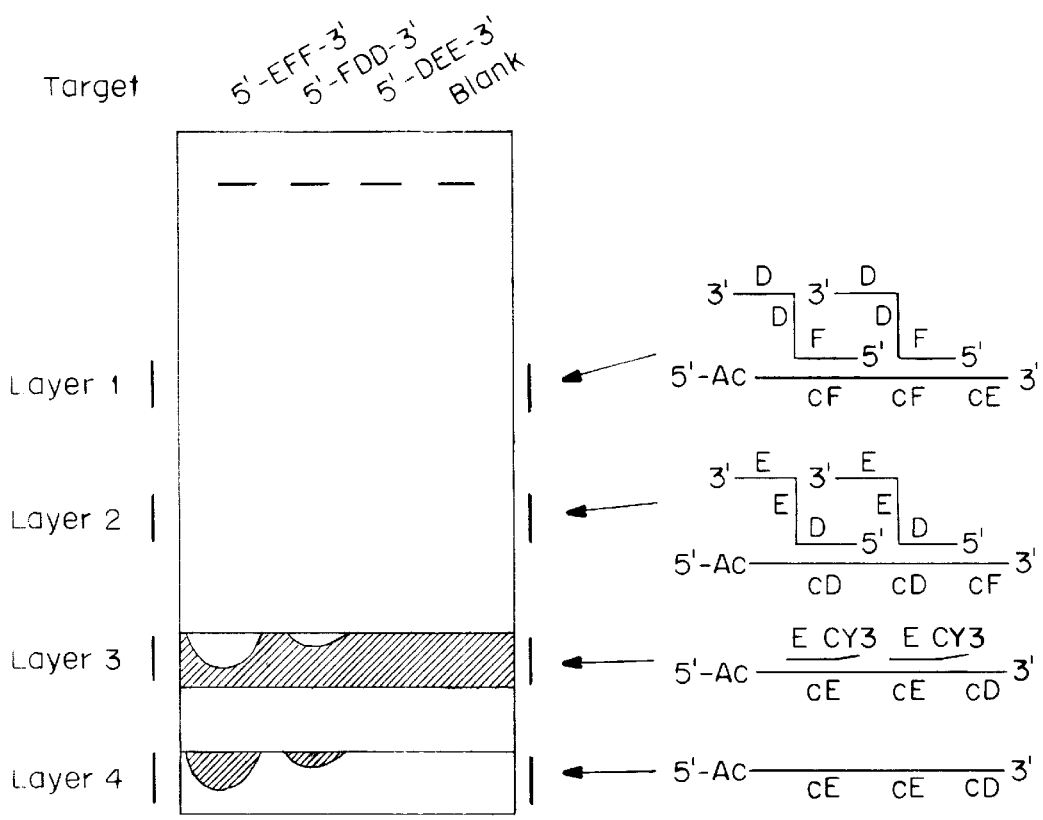
FIG. 10a is a polyacrylamide gel demonstrating the results of multiple sequential displacement reactions; also illustrated are stick figures depicting the polynucleotide sequence complexes.

Polynucleotide sequence DEE (lane 3) interacted only at the signal conversion layer (layer 3), thereby producing only two displaced signal polynucleotide sequences per target polynucleotide sequence. The FDD polynucleotide sequence (lane 2) was expected to displace two molecules of DEE at the second amplification layer (layer 2), based on affinity preferences, which will ultimately displace four signal polynucleotide sequences per initial target polynucleotide sequence. It is expected that each EFF polynucleotide sequence (lane 1) should displace two molecules from the first layer which will in turn displace four molecules from the second layer and subsequently displace eight molecules from the signal conversion layer. In FIG. 10a, the signals can be seen as positive images in the bottom layer (layer 4) and as negative images in the preceding layer (layer 3). The actual signals obtained at the final layer were quantified using a fluorescence scanner (Molecular Dynamic Fluorimager). The integrated fluorescent signals obtained from the capture layer (layer 4) for the three samples, EFF, FDD and DEE, were 10,400,000, 2,800,000 and 615,000 fluorescence units, respectively. Relative to the DEE signal, the observed signals show a ratio of 16.9(EFF):4.5(FDD):1 (DEE), in qualitative agreement with the predicted trend of 4:2:1, respectively.

Figure 10B:
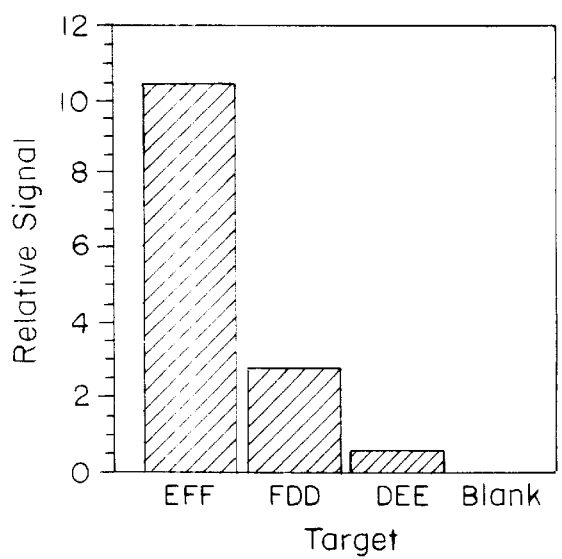
FIG. 10b is a bar graph representation of data obtained for multiple sequential displacement reactions.

FIG. 10b presents the data obtained in bar graph form such that comparative analysis can be performed. Target polynucleotide sequence EEF elicited the greatest signal response in the experiment. This response is in accord with the notion of multiple sequential displacement reactions promoting amplification of a signal. The response elicited by polynucleotide sequence DEE is the least out of all of the target polynucleotide sequences examined. The response of the DEE target is typical of a single step displacement reaction, hence the diminutive response. A method using single step displacement events was described in U.S. Pat. Nos. 4,766,062 and 4,766,064. This single step displacement cycle is in stark contrast to the multi-displacement cycle observed for target polynucleotide sequences EFF and FDD, which is the subject of the present invention.

Example 2

The Use of Temperature Gradient Gel Electrophoresis for Evaluating Polynucleotide Sequence Td During Electrophoresis The following example illustrates the general use of temperature gradient gels to estimate Td (the temperature at which 50% of the hybridization complex has dissociated during the time of electrophoresis) of a particular immobilized duplex (hybridization complex consisting of two polynucleotide sequences) under electrophoresis conditions. Deoxyribonucleic acid polynucleotide sequences were prepared by the phosphoramidite synthesis method and purified using size-exclusion and/or ion exchange chromatography, preferably, using High Performance Liquid Chromatography (HPLC; Operon, Integrated DNA Technologies, Almeda, Calif.). The sequence of the immobilized DNA polynucleotide sequence used was 5'-acrylamide-TTGGTTGGTTTATCGTTTTTG-3' (SEQ. ID. NO. 14). The 5' acrylamide moiety was added during automated synthesis using an acrylamide phosphoramidite (Acrydite™, Mosaic Technologies, Boston, Mass.). The labeled complementary polynucleotide sequence was 5'-CY3-CAAAAACGATAAACCAACCA-3' (SEQ. ID. NO. 15).

Polyacrylamide gels (22 cm×15.5 cm×0.75 cm) were prepared and poured in 3 sections, all containing 1×TBE. The acrylamide (BioRad) concentration was 12% (29:1 monomer to bis wt ratio). The top and bottom sections contained no polynucleotide sequence, while the center section (1 mL total volume) contained the immobilized polynucleotide sequence at 3 $\mu$M. Polymerization was catalyzed by the addition of 1/100th volume of 10% ammonium persulfate (APS) and 1/1000th volume of TEMED. To ensure smooth layers, the bottom and center layers were overlaid with 100% ethanol during polymerization. Gels were assembled in a single upright electrophoresis device (CBS Scientific).

Figure 11A:
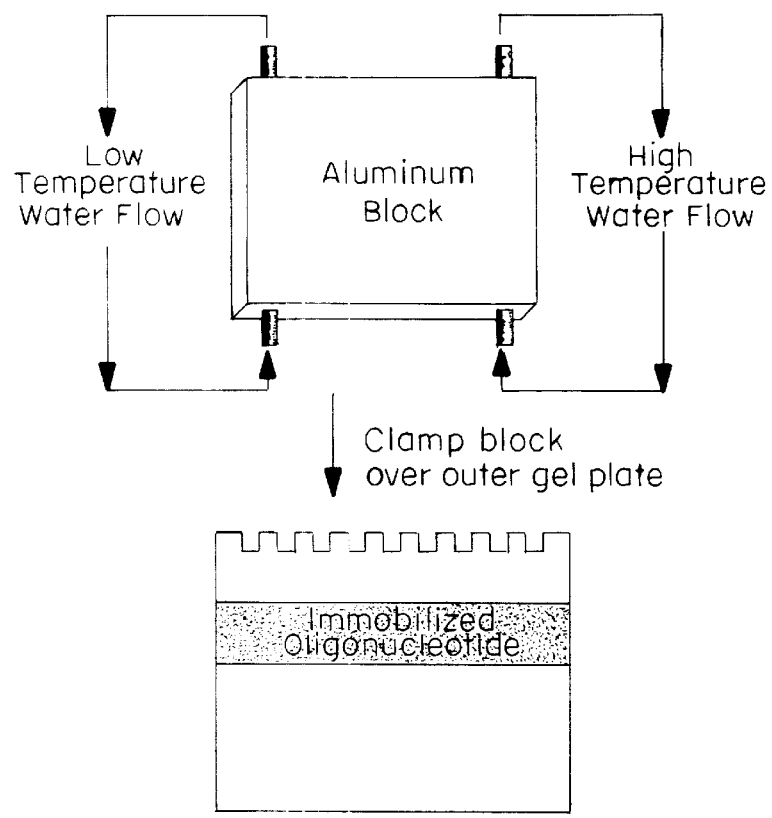
FIG. 11a is a schematic representation of a thermal gradient gel electrophoresis apparatus.

A temperature gradient from 35° C. to 65° C. was established across the gel by clamping to the glass plate an aluminum block through which low and high temperature water circulated on opposite ends. The temperature gradient thus obtained was measured by reading the temperature in each well of the gel with a thermistor and was found to be linear throughout the center of the gel. (See FIG. 11a).

The target polynucleotide sequence was diluted in gel loading buffer (8% sucrose, 1×TBE, bromophenol blue and xylene cyanol) and an equal amount (approximately 5 pmol) loaded in each lane. Electrophoresis was performed at 150 V for approximately one hour.

Figure 11B:
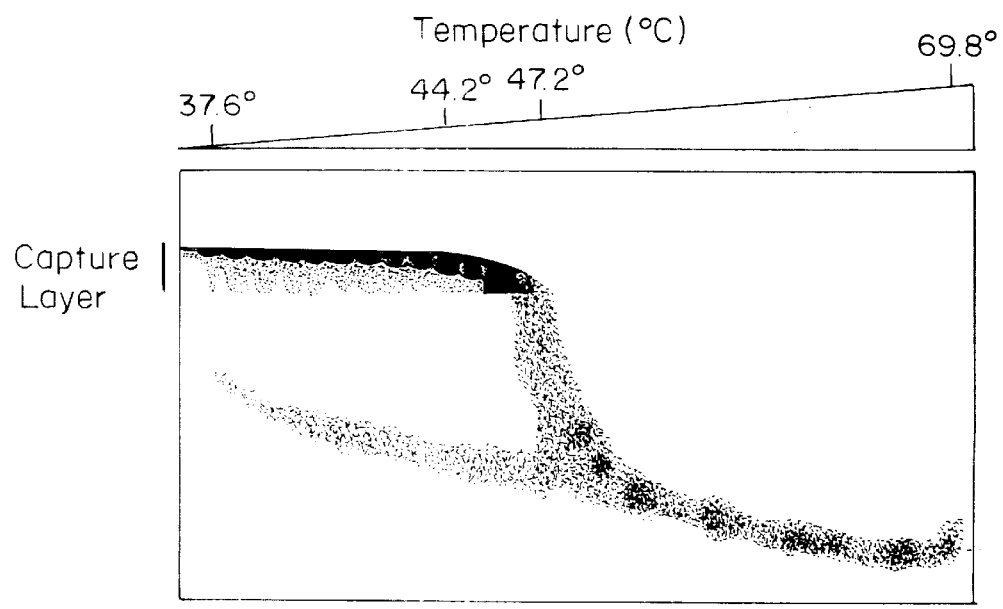
FIG. 11b is a fluorescent scan obtained from performing a thermal gradient gel electrophoresis.

Images were obtained by scanning gels on a Molecular Dynamics fluorimager. Fluorimetric analysis of the image allows determination of the position, and therefore, the temperature at which 50% of the labeled polynucleotide sequence is lost from the capture layer. This temperature represents the Td of the polynucleotide sequence hybrid at ta, the time used for electrophoresis. (See FIG. 11b).

Equivalents

While this invention has been particularly shown and described with references to preferred embodiments thereof, it will be understood by those skilled in the art that various changes in form and details may be made therein without departing from the spirit and scope of the invention as defined by the appended claims.

---

What is claimed is:

1. A method of detecting a target polynucleotide sequence in a biological sample comprising multiple sequential polynucleotide displacement for signal generation comprising the following steps:
   (a) forming a first probe complex by contacting a first polynucleotide sequence comprising a complementary target binding region (CTBR), with a second polynucleotide sequence comprising a partial target binding region (PTBR) and a cascade binding region (CBR), under conditions suitable for hybridization between said first and said second polynucleotide sequences, thereby forming a first probe complex;
   (b) forming a first displacement complex by contacting the complex of (a) with a target polynucleotide sequence comprising a target binding region (TBR), under conditions suitable for said target polynucleotide sequence to displace said second polynucleotide sequence and hybridize to said first polynucleotide sequence, thereby forming a first displacement complex and a displaced second polynucleotide sequence;
   (c) forming a second probe complex by contacting a fourth polynucleotide sequence comprising a complementary cascade binding region (CCBR), with a fifth polynucleotide sequence comprising at least one cascade binding region (CBR), under conditions suitable for hybridization between said fourth and fifth polynucleotide sequences, thereby forming a second probe complex; and
   (d) forming a second displacement complex by contacting the displaced second polynucleotide sequence of (b) with the second probe complex of (c) under conditions suitable for the displaced second polynucleotide sequence of (b) to displace said fifth polynucleotide sequence of (c) and hybridize with said fourth polynucleotide sequence of (c),
thereby producing a second displacement complex and a liberated fifth polynucleotide sequence which generates at least one signal, and wherein detection of the signal is indicative of the presence of the target polynucleotide sequence in a biological sample.

2. The method of claim 1, wherein said second polynucleotide sequence comprises multiple identical CBR and said fourth polynucleotide sequence comprises multiple identical CCBR, and wherein said fifth polynucleotide sequence comprises a CBR which is substantially identical to at least one of the CBR of said second polynucleotide sequence, thereby generating multiple signals via liberated fifth polynucleotide sequences per target polynucleotide sequence within a sample.

3. The method of claim 1, wherein the region of hybridization between the polynucleotide sequences is from about 5 to about 1000 nucleotides in length.

4. The method of claim 1, wherein the mode of detecting said signal is selected from the group consisting of: mass or density measurement, mass spectrometry, plasmon resonance, optical emission or absorption, fluorescence, phosphorescence, luminescence, chemiluminescence, polarization, refractive index changes, electrical conductivity, radioactivity, viscosity, turbidity and optical rotation.

5. The method of claim 1, wherein the assay is conducted in parallel, wherein in one assay the target polynucleotide sequence is absent and in the second parallel assay the target polynucleotide sequence is present, wherein the signal obtained for the assay without target polynucleotide sequence can be used to normalize the signal data obtained from the assay containing the target polynucleotide sequence.

6. A method of detecting a target polynucleotide sequence in a biological sample using a recursive cycle comprising multiple sequential polynucleotide displacement for signal generation comprising the following steps:
   (a) forming a first probe complex by contacting a first polynucleotide sequence comprising a first CTBR, with a second polynucleotide sequence comprising a first PTBR and a first CBR, under conditions suitable for hybridization between said first and said second polynucleotide sequences, thereby forming a first probe complex;
   (b) forming a first displacement complex by contacting the product of (a) with a target polynucleotide sequence comprising a TBR, under conditions suitable for said target polynucleotide sequence to displace said second polynucleotide sequence and hybridize to said first polynucleotide sequence, thereby forming a first displacement complex and a displaced second polynucleotide sequence;
   (c) forming a second probe complex by contacting a fourth polynucleotide sequence comprising a second CTBR and one or more first CCBR, with a fifth polynucleotide sequence comprising a second PTBR and one or more second CBR, wherein said second PTBR comprises a nucleotide sequence substantially identical to said first CBR, under conditions suitable for hybridization between said fourth and fifth polynucleotide sequence, thereby forming a second probe complex;
   (d) forming a second displacement complex by contacting the displaced second polynucleotide sequence of (b) with the product of (c), under conditions suitable for the displaced second polynucleotide sequence of (b) to displace said fifth polynucleotide sequence of (c) and hybridize with said fourth polynucleotide sequence of (c), thereby forming a second displacement complex and a displaced fifth polynucleotide sequence;
   (e) forming a third probe complex by contacting a sixth polynucleotide sequence comprising a third CTBR and one or more second CCBR, with a seventh polynucleotide sequence comprising a third PTBR and one or more third CBR, wherein said third PTBR comprises a nucleotide sequence substantially identical to said second CBR and said third CBR comprises a nucleotide sequence substantially identical to said TBR, under conditions suitable for hybridization between said sixth and seventh polynucleotide sequence, thereby forming a third probe complex; and
   (f) forming a third displacement complex by contacting the displaced fifth polynucleotide sequence of (d) with the product of (e), under conditions suitable for the displaced fifth polynucleotide sequence of (d) to displace said seventh polynucleotide sequence of (e) and hybridize with said sixth polynucleotide sequence of (e),
thereby liberating the seventh polynucleotide sequence which generates at least one signal and wherein detection of the signal is indicative of the presence of the target polynucleotide sequence in the biological sample.

7. The method of claim 6, wherein the region of hybridization between the polynucleotide sequences is from about 5 to about 1000 nucleotides in length.

8. The method of claim 6, wherein the mode of detecting said signal is selected from the group consisting of: mass or density measurement, mass spectrometry, plasmon resonance, optical emission or absorption, fluorescence, phosphorescence, luminescence, chemiluminescence, polarization, refractive index changes, electrical conductivity, radioactivity, viscosity, turbidity and optical rotation.

9. A method for detecting a target polynucleotide sequence in a biological sample, whereby at least two distinct signals are produced in response to a target polynucleotide sequence comprising multiple sequential polynucleotide displacement comprising the following steps:

(a) forming a first probe complex by contacting a first polynucleotide sequence comprising a CTBR, with a second polynucleotide sequence comprising a first PTBR and first and second CBR, wherein said first and second CBR comprise nucleotide sequences which are not substantially identical under conditions suitable for hybridization between said first and second polynucleotides, thereby forming a probe complex;

(b) forming a first displacement complex by contacting the complex of (a) with a target polynucleotide sequence comprising a TBR, under conditions suitable for said target polynucleotide sequence to displace said second polynucleotide sequence and hybridize to said first polynucleotide sequence, thereby forming a first displacement complex and a displaced second polynucleotide sequence;

(c) forming a second probe complex, wherein said second probe complex is heterogenous by contacting a fourth polynucleotide sequence comprising a CCBR, with a set of heterogenous polynucleotide sequences, the set comprising a fifth polynucleotide comprising a second PTBR and a third CBR, wherein said second PTBR comprises a nucleotide sequence substantially identical to said first CBR and a sixth polynucleotide sequence comprising a third PTBR and a fourth CBR, wherein said third PTBR comprises a nucleotide sequence substantially identical to the second CBR and, wherein said third and fourth CBR comprise nucleotide sequences which are not substantially identical, under conditions suitable for hybridization between said fourth polynucleotide sequence with said fifth and sixth polynucleotide sequences, thereby forming a second heterogenous probe complex; and (d) forming a second displacement complex, wherein said second displacement complex is heterogenous by contacting the displaced second polynucleotide sequence of (b) with the complex of (c), under conditions suitable for the displaced second polynucleotide sequence of (b) to displace said fifth and said sixth polynucleotide sequence of (c) and hybridize with said fourth polynucleotide sequence of (c), thereby liberating the fifth and sixth polynucleotide sequences which generate at least two different signals that are subject to detection and, wherein detection of at least one of the signals is indicative of the presence of the target polynucleotide sequence in the biological sample.

10. The method of claim 9 further comprising the steps of:

(e) forming multiple probe complexes by contacting sequences complementary to the fifth and sixth displaced polynucleotide sequences from step (d) with polynucleotide sequences comprising sequences partially complementary to said complementary sequences of the fifth and sixth polynucleotide sequences under conditions suitable for hybridization, thereby forming multiple probe complexes; and (f) forming multiple displacement complexes by contacting the multiple probe complexes of step (e) with said fifth and sixth displaced polynucleotide sequences from step (d) under conditions suitable for displacement and hybridization, thereby liberating two or more displaced polynucleotide sequences which generate multiple signals that are subject to detection and wherein detection of at least one of these signals is indicative of the presence of a target polynucleotide sequence in the biological sample.

11. The method of claim 9, wherein in step (c) there is a set of three or more heterogenous polynucleotide sequences that hybridize to said fourth polynucleotide sequence at distinct sites along said fourth polynucleotide sequence, and wherein these heterogenous polynucleotide sequences hybridized to said fourth polynucleotide sequence are subsequently displaced by said second polynucleotide sequence of step (b), thereby amplifying the assay signal generated from the displacement of these heterogenous polynucleotide sequences from the fourth polynucleotide sequence and wherein detection of at least one of these signals is indicative of the presence of a target polynucleotide sequence in the biological sample.

12. The method of claim 9, wherein the region of hybridization between the polynucleotide sequences is from about 5 to about 1000 nucleotides in length.

13. The method of claim 9, wherein the mode of detecting said signal is selected from the group consisting of: mass or density measurement, mass spectrometry, plasmon resonance, optical emission or absorption, fluorescence, phosphorescence, luminescence, chemiluminescence, polarization, refractive index changes, electrical conductivity, radioactivity, viscosity, turbidity and optical rotation.

14. A method of detecting two or more heterogenous target polynucleotide sequences in a biological sample comprising multiple sequential polynucleotide displacement for signal generation comprising the following steps:

(a) forming each member of a set of first probe complexes by
  (i) contacting a first polynucleotide sequence comprising a distinct CTBR, with a second polynucleotide sequence, wherein each said second polynucleotide sequence comprises a distinct PTBR, substantially identical first CBR and a substantially identical second CBR, under conditions suitable for hybridization between said first and second polynucleotide sequences, thereby forming a first probe complex; and
  (ii) repeating step (i) until the desired number of probe complexes have been formed for the desired number of target polynucleotide sequences in the sample, thereby forming a set of first probe complexes;

(b) forming a set of first displacement complexes by (i) contacting the complexes of (a) with their respective target polynucleotide sequence under conditions suitable for said target polynucleotide sequence to displace at least one second polynucleotide sequence of (a) and hybridize to said first polynucleotide sequence of (a), thereby forming a first displacement complex; and
  (ii) repeating (i) until all desired displacement complexes are formed, thereby forming a set of first displacement complexes and displaced second polynucleotide sequences;

(c) forming a second probe complex by contacting a fourth polynucleotide sequence comprising a CCBR, wherein said CCBR is complementary to both said first CBR and said second CBR, with a fifth polynucleotide sequence comprising a third CBR, wherein said third CBR comprises a nucleotide sequence substantially identical to said second CBR, under conditions suitable for hybridization between said fourth and fifth polynucleotide sequences, thereby forming a second probe complex; and (d) forming a second displacement complex by contacting the displaced second polynucleotide sequence of (b) with the complex of (c) under conditions suitable for said displaced second polynucleotide sequences of (b) to displace said fifth polynucleotide sequence of (c) and hybridize with said fourth polynucleotide sequence of (c), thereby forming a second displacement complex and displaced fifth polynucleotide sequence;

thereby liberating a fifth polynucleotide sequence which generates at least one homogenous signal for two or more heterogenous target polynucleotide sequences assayed and wherein detection of the signal is indicative of the presence of at least one heterogenous target polynucleotide sequence in the biological sample.

15. The method of claim 14, wherein the region of hybridization between the polynucleotide sequences is from about 5 to about 1000 nucleotides in length.

16. The method of claim 14, wherein the mode of detecting said signals is selected from the group consisting of: mass or density measurement, mass spectrometry, plasmon resonance, optical emission or absorption, fluorescence, phosphorescence, luminescence, chemiluminescence, polarization, refractive index changes, electrical conductivity, radioactivity, viscosity, turbidity and optical rotation.

17. A method for detecting a target polynucleotide sequence in a biological sample using an immobilized probe comprising multiple sequential polynucleotide displacement for signal generation comprising the steps of:

(a) immobilizing a first polynucleotide probe to a first surface wherein the probe comprises a CTBR;

(b) forming a first immobilized probe complex by contacting a second polynucleotide comprising a PTBR and a CBR, with the immobilized probe under conditions suitable for hybridization between said first and second polynucleotide sequences, wherein the complex formed by the hybridization of said first and second polynucleotide sequence is immobilized, thereby forming a first immobilized probe complex;

(c) forming a first immobilized displacement complex by contacting said immobilized complex of (a) with a target polynucleotide sequence comprising a TBR, under conditions suitable for said target polynucleotide sequence to displace said second polynucleotide sequence from said immobilized complex of (a) and hybridize to said first polynucleotide sequence of said immobilized complex of (a), thereby forming a first immobilized displacement complex and a displaced second polynucleotide sequence;

(d) immobilizing a fourth polynucleotide probe to a second surface, wherein the fourth polynucleotide probe comprises at least one CCBR;

(e) forming a second immobilized probe complex by contacting said fourth polynucleotide sequence with a fifth polynucleotide sequence comprising at least one CBR, under conditions suitable for hybridization between said fourth and fifth polynucleotide sequences thereby forming a second immobilized displacement complex;

(f) transferring said displaced second polynucleotide sequence from said first surface to a second surface;

(g) forming a second immobilized displacement complex by contacting said immobilized complex of (e) with said second polynucleotide sequence under conditions suitable for said second polynucleotide sequence to displace said fifth polynucleotide sequence from said immobilized complex of (e) and hybridize to said fourth polynucleotide sequence of said immobilized complex of (e), thereby forming a second immobilized displacement complex and a displaced fifth polynucleotide sequence, wherein the fifth polynucleotide sequence generates at least one signal and wherein detection of the signal is indicative of the presence of the target polynucleotide sequence in the biological sample using an immobilized probe.

18. The method of claim 17, wherein the region of hybridization between the polynucleotide sequences is from about 5 to about 1000 nucleotides in length.

19. The method of claim 17, wherein the mode of detecting said signal is selected from the group consisting of: mass or density measurement, mass spectrometry, plasmon resonance, optical emission or absorption, fluorescence, phosphorescence, luminescence, chemiluminescence, polarization, refractive index changes, electrical conductivity, radioactivity, viscosity, turbidity and optical rotation.

20. The method of claim 17, further comprising additional surfaces.

21. The method of claim 20 further comprising the step of:

(h) repeating steps (c), (d), (e), (f) and (g), wherein additional cycles of displacement and transfer are performed using additional polynucleotide sequences.

22. The method of claim 17, wherein the means for said transfer from the first to second surface is selected from the group consisting of: pipetting, counter current distribution, gravitational flow, electrically induced endosmotic flow, wetting, capillary action, pump-mediated flow, electrophoresis, chromatographic, filtration, centrifugation and decantation.

23. The method of claim 17, wherein the means for the immobilization of polynucleotide sequence complexes comprises adsorption, covalent bonds, ionic bonds and/or affinity-ligand complexes.

24. The method of claim 23, wherein said immobilized polynucleotide sequence has covalently attached to it an acrylamide moiety.

25. The method of claim 23, wherein the polynucleotide sequence of said first or second immobilized probe complex is coextensively linked to an affinity ligand, wherein said affinity ligand interacts with its cognate receptor which itself is coextensively linked to a magnetic particle forming a magnetic particle complex, wherein when a magnetic field is applied to the surface containing said magnetic particle complex, the magnetic particle is immobilized to said surface, thereby immobilizing the entire magnetic particle complex.

26. The method of claim 20, wherein said surfaces are coextensive and separated by a size-selective partition or membrane.

27. The method of claim 26, wherein said size-selective partition or membrane allows for only the transfer of displaced polynucleotide sequences having the proper size from one surface to an adjoining surface through said size-selective partition or membrane.

28. The method of claim 27, wherein said transfer is accomplished by any means selected from the group consisting of: diffusion, pump-mediated flow, gravitational flow, electrically induced endosmotic flow, wetting, capillary action and electrophoresis.

29. The method of claim 17, wherein at least one of said first or second surface comprises a solid support matrix comprising multiple reaction states spatially positioned within the matrix.

30. The method of claim 29, wherein the displaced polynucleotide sequence generated from a displacement complex in one reaction station migrates through the matrix or is transferred by mechanical means, thereby effecting transfer of the displacement product from one reaction station to the next.

31. The method of claim 30, wherein said migration through the matrix is facilitated by, gravitational flow, electrophoresis, electrically induced endosmotic flow, wetting, capillary action and pump flow.

32. The method of claim 30, wherein said mechanical transfer is facilitated by pipetting.

33. The method of claim 30, wherein the solid support is selected from a group consisting of: chromatographic supports, thin-layer plates and membranes, polyacrylamide gels, starch gels, agarose gels and other polymeric gels.

34. A method for signal generation by multiple sequential displacement reactions using polynucleotide sequences immobilized in a polyacrylamide solid support matrix comprising independent layers of co-polymerized products, wherein the layers are arranged in the matrix proximal to distal relative to the target sample wells, comprising multiple sequential polynucleotide displacement for signal generation, comprising the following steps:

(a) forming a first probe complex comprising contacting a first polynucleotide sequence comprising an acrylamide moiety bound to said first polynucleotide sequence and a CTBR, with a second polynucleotide sequence comprising a PTBR and CBR, under conditions suitable for hybridization between said first and second polynucleotide sequences, thereby forming a first probe complex;

(b) forming a second probe complex comprising contacting a third polynucleotide sequence comprising an acrylamide moiety bound to said third polynucleotide sequence and a CCBR, with a fourth polynucleotide sequence comprising at least two heterogenous CBR, under conditions suitable for hybridization between said third and fourth polynucleotide sequences, thereby forming a second probe complex;

(c) forming a third probe complex comprising contacting a fifth polynucleotide sequence comprising an acrylamide moiety bound to said fifth polynucleotide sequence and a CCBR, partially or fully complementary to said fourth polynucleotide sequence with a labeled sixth polynucleotide sequence comprising at least one CBR, under conditions suitable for hybridization between said fifth and labeled sixth polynucleotide sequences, thereby forming a third probe complex;

(d) forming immobilized probe complex layers with a polyacrylamide solid support matrix by contacting the complexes of (a) through (c) individually with polyacrylamide under conditions suitable for co-polymerization, wherein co-polymerization occurs between each displacement complex comprising said acrylamide moiety and polyacrylamide, and wherein each co-polymerized product is then poured into individual horizontal slots within a precast polyacrylamide gel, thereby forming independent layers of co-polymerized complexes following the order of (a) to (c) wherein (a) is the complex most proximal to the target sample well(s) and (c) is the most distal within the polyacrylamide support matrix, (e) removing non-immobilized first polynucleotide sequences and excess second polynucleotide sequences by applying an electric field gradient to the polyacrylamide gel and performing electrophoresis, thereby removing all non-immobilized species of polynucleotide sequences from the polyacrylamide solid support matrix; and (f) performing analysis on a target polynucleotide sequences, or set of target polynucleotide sequences, by re-orienting the polyacrylamide gel such that said sample target polynucleotide sequences are loaded perpendicular to the long axis of the displacement complex layers and applying an electric field gradient to the polyacrylamide gel, thereby facilitating the electrophoresis of said sample target polynucleotide sequences longitudinally through the displacement layers sequentially;

thereby generating multiple sequential polynucleotide displacement wherein at least one signal from the liberated labeled sixth polynucleotide sequence is subject to detection and wherein at least one signal is indicative of at least one target polynucleotide sequence assayed.

35. The method of claim 34, wherein said acrylamide moiety is covalently attached to the 5'-end of the polynucleotide sequence.

36. The method of claim 34, wherein said acrylamide moiety is covalently attached in any region of the modified polynucleotide sequence.

37. The method of claim 34, wherein said signal generated from the sixth polynucleotide sequence is detected using a fluorescent scanner.

38. A diagnostic kit for determining the presence or absence of a target polynucleotide sequence within a biological sample comprising:

(i) a first probe complex comprising a first polynucleotide sequence comprising a CTBR, hybridized to a second polynucleotide sequence comprising a PTBR and a CBR, and (ii) a second probe complex comprising a third polynucleotide sequence, comprising a CCBR hybridized to a labeled fourth polynucleotide sequence.

39. The diagnostic kit of claim 38, wherein the region of hybridization between the polynucleotide sequences is from about 5 to about 1000 nucleotides in length.

40. The diagnostic kit of claim 38, wherein the mode of detecting the signal is selected from the group consisting of: mass or density measurement, mass spectrometry, plasmon resonance, optical emission or absorption, fluorescence, phosphorescence, luminescence, chemiluminescence, polarization, refractive index changes, electrical conductivity, radioactivity, viscosity, turbidity and optical rotation.

41. The diagnostic kit of claim 38, wherein said labeled fourth polynucleotide sequence is bonded to a moiety detectable by light emission or absorption.

42. The diagnostic kit of claim 38, wherein said label is a radioactive label.

43. The diagnostic kit of claim 38, wherein said label is a fluorescence label.

44. The diagnostic kit of claim 38, wherein said fourth polynucleotide sequence is bonded to an affinity reagent label.

45. The diagnostic kit of claim 44, wherein the affinity reagent is biotin.

46. The method of claim 1, further comprising forming additional probe and displacement complexes, wherein each displacing polynucleotide comprises at least two CBR.

47. The method of claim 46, wherein the CBR are substantially identical.

48. The method of claim 46, wherein the CBR are not substantially identical.

49. The method of claim 46, further comprising additional CBR.

50. The method of claim 46, wherein the number of additional probe and displacement complexes is selected from the group consisting of 1, 2, 3 and 4 probe and displacement complexes.

51. The method of claim 1, further comprising contacting a probe complex of (a) with a displaced fifth polynucleotide sequence of (d) and repeating at least steps (a) and (b) of the method, thereby generating additional multiple displacement reactions in a successive cycle.

52. The method of claim 51 comprising multiple successive cycles.

53. The method of claim 6, further comprising contacting a probe complex of (a) with a displaced seventh polynucleotide sequence of (e) and repeating at least steps (a) through (b) of the method, thereby generating additional multiple displacement reactions in a successive cycle.

54. The method of claim 53 comprising multiple successive cycles.

55. The method of claim 9, further comprising forming additional probe and displacement complexes for additional signal generation.

56. The method of claim 9, wherein more than two signals are produced for each target polynucleotide detected in the biological sample.

57. The method of claim 9, further comprising the steps of:
- (e) forming a third probe complex by contacting an eighth polynucleotide sequence comprising a second CTBR, with a seventh polynucleotide sequence comprising a fifth CBR, wherein said fifth CBR comprises a nucleotide sequence substantially identical to said third CBR, under conditions suitable for hybridization between said seventh and eighth polynucleotide sequences, thereby forming a third probe complex;
- (f) forming a fourth probe complex by contacting a tenth polynucleotide sequence comprising a third CTBR, with a ninth polynucleotide sequence comprising a sixth CBR, wherein said sixth CBR comprises a nucleotide sequence which is substantially identical to said fourth CBR but not to said third CBR, under conditions suitable for hybridization between said ninth and tenth polynucleotide sequences, thereby forming a fourth probe complex;
- (g) forming a third displacement complex by contacting the displaced fifth polynucleotide sequence of (d) with the complex of (e) under conditions suitable for said displaced fifth polynucleotide sequence of (d) to displace said seventh polynucleotide and hybridize to said eighth polynucleotide;
- (h) forming a fourth displacement complex by contacting the displaced sixth polynucleotide sequence of (d) with the complex of (f) under conditions suitable for said displaced sixth polynucleotide sequence of (d) to displace said ninth polynucleotide sequence and hybridize to said tenth polynucleotide sequence; and thereby liberating seventh and ninth polynucleotide sequence and detecting either the seventh or the ninth polynucleotide sequence, wherein detection of the signal is indicative of the presence of at least one target polynucleotide sequence in the biological sample.

\* \* \* \* \*

SEQUENCE LISTING

<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<223> OTHER INFORMATION: synthesized oligonucleotide

<400> SEQUENCE: 1
gtgcggaagg agtgatgtaa                    20

<210> SEQ ID NO 2
<211> LENGTH: 20
<212> TYPE: DNA
<213> ORGANISM: Artificial Sequence
<220> FEATURE:
<223> OTHER INFORMATION: synthesized oligonucleotide

<400> SEQUENCE: 2
caaaaacgat aaaccaacca                    20

<210> SEQ ID NO 3
<211> LENGTH: 20
<212> TYPE: DNA
<213> ORGANISM: Artificial Sequence
<220> FEATURE:
<223> OTHER INFORMATION: synthesized oligonucleotide

<400> SEQUENCE: 3
aatggagaaa gacggagagc                    20

<210> SEQ ID NO 4
<211> LENGTH: 20
<212> TYPE: DNA
<213> ORGANISM: Artificial Sequence
<220> FEATURE:
<223> OTHER INFORMATION: synthesized oligonucleotide

<400> SEQUENCE: 4
ttacatcact ccttccgcac                                          20

<210> SEQ ID NO 5
<211> LENGTH: 20
<212> TYPE: DNA
<213> ORGANISM: Artificial Sequence
<220> FEATURE:
<223> OTHER INFORMATION: synthesized oligonucleotide

<400> SEQUENCE: 5
tggttggttt atcgtttttg                                          20

<210> SEQ ID NO 6
<211> LENGTH: 20
<212> TYPE: DNA
<213> ORGANISM: Artificial Sequence
<220> FEATURE:
<223> OTHER INFORMATION: Synthesized oligonucleotide

<400> SEQUENCE: 6
gctctccgtc tttctccatt                                          20

<210> SEQ ID NO 7
<211> LENGTH: 20
<212> TYPE: DNA
<213> ORGANISM: Artificial Sequence
<220> FEATURE:
<223> OTHER INFORMATION: synthesized oligonucleotide

<400> SEQUENCE: 7
caaaaacgat aaaccaacca                                          20

<210> SEQ ID NO 8
<211> LENGTH: 60
<212> TYPE: DNA
<213> ORGANISM: Artificial Sequence
<220> FEATURE:
<223> OTHER INFORMATION: synthesized oligonucleotide

<400> SEQUENCE: 8
aatggagaaa gacggagagc gtgcggaagg agtgatgtaa gtgcggaagg agtgatgtaa     60

<210> SEQ ID NO 9
<211> LENGTH: 60
<212> TYPE: DNA
<213> ORGANISM: Artificial Sequence
<220> FEATURE:
<223> OTHER INFORMATION: Synthesized oligonucleotide

<400> SEQUENCE: 9
gtgcggaagg agtgatgtaa caaaaacgat aaaccaacca caaaaacgat aaaccaacca     60

<210> SEQ ID NO 10
<211> LENGTH: 62
<212> TYPE: DNA
<213> ORGANISM: Artificial Sequence
<220> FEATURE:

<223> OTHER INFORMATION: synthesized oligonucleotide

<400> SEQUENCE: 10
caaaaacgat aaaccaacca aatggagaaa gacggagaga gcaatggaga aagacggaga    60
gc    62

<210> SEQ ID NO 11
<211> LENGTH: 60
<212> TYPE: DNA
<213> ORGANISM: Artificial Sequence
<220> FEATURE:
<223> OTHER INFORMATION: synthesized-modified oligonucleotides
      acrylamide polynucleotides

<400> SEQUENCE: 11
tggttggttt atcgtttttg tggttggttt atcgtttttg ttacatcact ccttccgcac    60

<210> SEQ ID NO 12
<211> LENGTH: 60
<212> TYPE: DNA
<213> ORGANISM: Artificial Sequence
<220> FEATURE:
<223> OTHER INFORMATION: synthesized-modified oligonucleotides
      acrylamide polynucleotides

<400> SEQUENCE: 12
gctctccgtc tttctccatt gctctccgtc tttctccatt caaaaacgat aaaccaacca    60

<210> SEQ ID NO 13
<211> LENGTH: 60
<212> TYPE: DNA
<213> ORGANISM: Artificial Sequence
<220> FEATURE:
<223> OTHER INFORMATION: synthesized-modified oligonucleotides
      acrylamide polynucleotides

<400> SEQUENCE: 13
ttacatcact ccttccgcac ttacatcact ccttccgcac gctctccgtc tttctccatt    60

<210> SEQ ID NO 14
<211> LENGTH: 21
<212> TYPE: DNA
<213> ORGANISM: Artificial Sequence
<220> FEATURE:
<223> OTHER INFORMATION: synthesized oligonucleotide
      modified with acrylamide

<400> SEQUENCE: 14
ttggttggtt tatcgttttt g    21

<210> SEQ ID NO 15
<211> LENGTH: 20
<212> TYPE: DNA
<213> ORGANISM: Artificial Sequence
<220> FEATURE:
<223> OTHER INFORMATION: synthesized oligonucleotide
      modified with label

<400> SEQUENCE: 15
caaaaacgat aaaccaacca    20